United States Patent
Ohsumi et al.

(10) Patent No.: US 11,617,790 B2
(45) Date of Patent: Apr. 4, 2023

(54) METHOD FOR TREATING CANCER USING ARTIFICIAL ADJUVANT CELL (AAVC)

(71) Applicants: ASTELLAS PHARMA INC., Tokyo (JP); RIKEN, Saitama (JP)

(72) Inventors: Keisuke Ohsumi, Tokyo (JP); Taku Yoshida, Tokyo (JP); Masayuki Kanki, Tokyo (JP); Shinichiro Fujii, Saitama (JP); Kanako Shimizu, Saitama (JP)

(73) Assignees: Astellas Pharma Inc., Tokyo (JP); RIKEN, Saitama (JP)

( * ) Notice: Subject to any disclaimer, the term of this patent is extended or adjusted under 35 U.S.C. 154(b) by 0 days.

(21) Appl. No.: 17/312,363

(22) PCT Filed: Dec. 1, 2020

(86) PCT No.: PCT/JP2020/044587
§ 371 (c)(1),
(2) Date: Jun. 9, 2021

(87) PCT Pub. No.: WO2021/112056
PCT Pub. Date: Jun. 10, 2021

(65) Prior Publication Data
US 2022/0016239 A1   Jan. 20, 2022

(30) Foreign Application Priority Data
Dec. 2, 2019 (JP) .............................. JP2019-217712

(51) Int. Cl.
*A61K 35/22* (2015.01)
*A61K 39/00* (2006.01)
*A61K 39/39* (2006.01)

(52) U.S. Cl.
CPC .............. *A61K 39/39* (2013.01); *A61K 35/22* (2013.01)

(58) Field of Classification Search
CPC .................................................... A61K 39/39
See application file for complete search history.

(56) References Cited

U.S. PATENT DOCUMENTS

| | | | |
|---|---|---|---|
| 9,783,821 B2 * | 10/2017 | Fujii .............. | A61K 39/001153 |
| 10,316,332 B2 * | 6/2019 | Fujii .................. | A61K 39/0011 |
| 11,072,802 B2 * | 7/2021 | Fujii ...................... | C07K 14/82 |
| 2010/0233215 A1 | 9/2010 | Fujii et al. | |
| 2011/0280895 A1 | 11/2011 | Fujii et al. | |
| 2013/0189302 A1 * | 7/2013 | Fujii ...................... | A61K 39/12 424/204.1 |
| 2014/0179004 A1 | 6/2014 | Fujii et al. | |

FOREIGN PATENT DOCUMENTS

| WO | WO-2007/097370 A1 | 8/2007 |
| WO | WO-2010/061930 A1 | 6/2010 |
| WO | WO-2013/018778 A1 | 2/2013 |

OTHER PUBLICATIONS

Ishikawa et al (Clinical Cancer Research, 2005, 11:1910-1917).*
Uchida et al (Cancer Immuno. Immunother., 2008, 57:337-345).*
Motohashi et al (Journal of Immunology, 2009, 182:2492-2501).*
Sainz et al (Acta Biomaterialia, 2018, 76:193-207).*
Notice of Allowance dated Jun. 29, 2021 in JP 2021-513476.
Office Action dated Jun. 15, 2021 in JP 2021-513476 with English translation.
Bai et al., "Lysosomal recycling terminates CD1d-mediated presentation of short and polyunsaturated variants of the NKT cell lipid antigen alphaGalCer," PNAS, Jun. 23, 2009, 106(25):10254-10259.
Fujii et al., "Prolonged IFN-gamma-producing NKT response induced with alpha-galactosylceramide-loaded DCs,"Aug. 5, 2002, Nature Immunology, 3(9):867-874.
Giaccone et al., "A Phase I Study of the Natural Killer T-Cell Ligand alpha-Galactosylceramide (KRN7000) in Patients with Solid Tumors," Clinical Cancer Research, Dec. 2002, 8(12):3702-3709.
Hasegawa et al., "Liver Injury After Invariant NKT Cell Activation by Free Alpha-galactosylceramide and Alpha-galactosylceramide-loaded Dendritic Cells," Anticancer Research, 2016, 36:3667-3672.
International Search Report dated Feb. 2, 2021 in PCT/JP2020/044587.
Ishikawa et al., "A Phase I Study of alpha-Galactosylceramide (KRN7000)-Pulsed Dendritic Cells in Patients with Advanced and Recurrent Non-Small Cell Lung Cancer," Clinical Cancer Research, Mar. 1, 2005, 11:1910-1917.
Motohashi et al., "A Phase I-II Study of alpha-Galactosylceramide-Pulsed IL-2/GM-CSF-Cultured Peripheral Blood Monunuclear Cells in Patients with Advanced and Recurrent Non-Small Cell Lung Cancer," The Journal of Immunology, Feb. 15, 2009, 182(4):2492-2501.
Shimizu et al., "Systemic DC Activation Modulates the Tumor Microenvironment and Shapes the Long-Lived Tumor-Specific Memory Mediated by CD8 T Cells," Cancer Research, Jul. 1, 2016, 76(13):3756-3766.
Shimizu et al., "Vaccination with Antigen-Transfected, NKT Cell Ligand-Loaded, Human Cells Elicits Robust In Situ Immune Responses by Dendritic Cells," Cancer Research, Oct. 29, 2012, 73(1):62-73.

(Continued)

*Primary Examiner* — Laura B Goddard
(74) *Attorney, Agent, or Firm* — Foley & Lardner LLP

(57) ABSTRACT

[Problem to be Solved]
Provided is an effective and safe method for treating or preventing a cancer using aAVC.
[Solution]
The present invention finds suitable ranges of the dose of α-GalCer loaded on aAVC cell surface, and the amount of α-GalCer loaded on aAVC cell surface in a pharmaceutical composition comprising aAVC, which are preferred in terms of securing effectiveness and safety in the treatment and prevention of a cancer using aAVC, and provides an effective and safe method for treating or preventing a cancer using aAVC, aAVC for effective and safe treatment or prevention of a cancer, and a pharmaceutical composition comprising the same, etc.

3 Claims, 3 Drawing Sheets
Specification includes a Sequence Listing.

(56) References Cited

OTHER PUBLICATIONS

Toura et al., "Cutting Edge: Inhibition of Experimental Tumor Metastasis by Dendritic Cells Pulsed with alpha-Galactosylceramide," J. Immunol., Sep. 1, 1999, 163(5):2387-2391.
Office Action dated May 11, 2021, in JP 2021-513476, with English translation.

* cited by examiner

1. Results of measuring body weight of male mouse in a single-dose toxicity study in mice 2. Results of measuring body weight of female mouse in a single-dose toxicity study in mice 1. Results of measuring food consumption of male mouse in a single-dose toxicity study in mice 2. Results of measuring food consumption of female mouse in a single-dose toxicity study in mice

SEQUENCE LISTING

<160> NUMBER OF SEQ ID NOS: 6

<210> SEQ ID NO 1
<211> LENGTH: 1554
<212> TYPE: DNA

```
<213> ORGANISM: Artificial Sequence
<220> FEATURE:
<223> OTHER INFORMATION: Synthetic nucleic acid encoding human WT1
<220> FEATURE:
<221> NAME/KEY: CDS
<222> LOCATION: (1)..(1554)

<400> SEQUENCE: 1 atg cag gac cct gcc agc aca tgt gtg cct gag cct gcc agc cag cac        48
Met Gln Asp Pro Ala Ser Thr Cys Val Pro Glu Pro Ala Ser Gln His
1               5                   10                  15 acc ctg aga tct ggc cct gga tgc ctg cag cag cct gaa cag cag ggc        96
Thr Leu Arg Ser Gly Pro Gly Cys Leu Gln Gln Pro Glu Gln Gln Gly
            20                  25                  30 gtg cgc gat cct ggc gga att tgg gcc aaa ctg gga gcc gcc gaa gcc       144
Val Arg Asp Pro Gly Gly Ile Trp Ala Lys Leu Gly Ala Ala Glu Ala
        35                  40                  45 agc gct gaa aga ctg cag ggc aga aga agc aga ggc gcc agc gga tct       192
Ser Ala Glu Arg Leu Gln Gly Arg Arg Ser Arg Gly Ala Ser Gly Ser
    50                  55                  60 gag ccc cag cag atg gga tct gac gtg cgg gac ctg aat gcc ctg ctg       240
Glu Pro Gln Gln Met Gly Ser Asp Val Arg Asp Leu Asn Ala Leu Leu
65                  70                  75                  80 cct gct gtg cct tct ctg ggc gga ggc gga gga tgt gct ctg cct gtg       288
Pro Ala Val Pro Ser Leu Gly Gly Gly Gly Cys Ala Leu Pro Val
                85                  90                  95 tct ggc gct gct cag tgg gct ccc gtg ctg gat ttt gct cct cct ggc       336
Ser Gly Ala Ala Gln Trp Ala Pro Val Leu Asp Phe Ala Pro Pro Gly
            100                 105                 110 gct tct gcc tac ggc tct ctg gga gga cct gct cct cca cca gct cca       384
Ala Ser Ala Tyr Gly Ser Leu Gly Gly Pro Ala Pro Pro Pro Ala Pro
        115                 120                 125 cct cca ccc cct cca cca ccc cca cac agc ttc atc aag cag gaa cct       432
Pro Pro Pro Pro Pro Pro Pro His Ser Phe Ile Lys Gln Glu Pro
    130                 135                 140 agc tgg ggc gga gcc gag cct cac gag gaa cag tgt ctg agc gcc ttc       480
Ser Trp Gly Gly Ala Glu Pro His Glu Glu Gln Cys Leu Ser Ala Phe
145                 150                 155                 160 acc gtg cac ttc agc ggc cag ttt acc ggc aca gcc ggc gct tgt aga       528
Thr Val His Phe Ser Gly Gln Phe Thr Gly Thr Ala Gly Ala Cys Arg
                165                 170                 175 tac ggc cct ttt ggc cca cct ccc cca agc cag gca tct agc gga cag       576
Tyr Gly Pro Phe Gly Pro Pro Pro Ser Gln Ala Ser Ser Gly Gln
            180                 185                 190 gcc aga atg ttc ccc aac gcc ccc tac ctg cct agc tgc ctg gaa agc       624
Ala Arg Met Phe Pro Asn Ala Pro Tyr Leu Pro Ser Cys Leu Glu Ser
        195                 200                 205 cag ccc gcc atc aga aac cag ggc tac agc acc gtg acc ttc gac ggc       672
Gln Pro Ala Ile Arg Asn Gln Gly Tyr Ser Thr Val Thr Phe Asp Gly
    210                 215                 220 aca cct agc tac ggc cac acc cct tct cat cac gcc gcc cag ttc ccc       720
Thr Pro Ser Tyr Gly His Thr Pro Ser His His Ala Ala Gln Phe Pro
225                 230                 235                 240 aat cac tcc ttc aag cac gag gac ccc atg ggc cag cag gga agc ctg       768
Asn His Ser Phe Lys His Glu Asp Pro Met Gly Gln Gln Gly Ser Leu
                245                 250                 255 gga gag cag cag tac agc gtg ccc cct cct gtg tac ggc tgt cac acc       816
Gly Glu Gln Gln Tyr Ser Val Pro Pro Pro Val Tyr Gly Cys His Thr
            260                 265                 270 cct acc gat agc tgc aca ggc agc cag gct ctg ctg ctg aga acc ccc       864
Pro Thr Asp Ser Cys Thr Gly Ser Gln Ala Leu Leu Leu Arg Thr Pro
```

-continued

```
                275                 280                 285
tac agc agc gac aac ctg tac cag atg acc agc cag ctg gaa tgc atg      912
Tyr Ser Ser Asp Asn Leu Tyr Gln Met Thr Ser Gln Leu Glu Cys Met
    290                 295                 300 acc tgg aac cag atg aac ctg ggc gcc acc ctg aaa ggc gtg gcc gct      960
Thr Trp Asn Gln Met Asn Leu Gly Ala Thr Leu Lys Gly Val Ala Ala
305                 310                 315                 320 gga tct agc agc tcc gtg aag tgg aca gag ggc cag agc aac cac agc     1008
Gly Ser Ser Ser Ser Val Lys Trp Thr Glu Gly Gln Ser Asn His Ser
                325                 330                 335 acc ggc tac gag tcc gac aac cac acc acc cct atc ctg tgc gga gcc     1056
Thr Gly Tyr Glu Ser Asp Asn His Thr Thr Pro Ile Leu Cys Gly Ala
            340                 345                 350 cag tac aga atc cac acc cac ggc gtg ttc cgg gga atc cag gat gtg     1104
Gln Tyr Arg Ile His Thr His Gly Val Phe Arg Gly Ile Gln Asp Val
        355                 360                 365 cgg aga gtg cct ggc gtg gcc cct aca ctc gtg cgc tct gcc tct gag     1152
Arg Arg Val Pro Gly Val Ala Pro Thr Leu Val Arg Ser Ala Ser Glu
    370                 375                 380 aca agc gag aag cgg ccc ttc atg tgc gcc tac ccc ggc tgc aac aag     1200
Thr Ser Glu Lys Arg Pro Phe Met Cys Ala Tyr Pro Gly Cys Asn Lys
385                 390                 395                 400 cgg tac ttc aag ctg agc cat ctg cag atg cac agc aga aag cac acc     1248
Arg Tyr Phe Lys Leu Ser His Leu Gln Met His Ser Arg Lys His Thr
                405                 410                 415 ggc gag aag ccc tac cag tgc gac ttc aag gac tgc gag cgg cgg ttc     1296
Gly Glu Lys Pro Tyr Gln Cys Asp Phe Lys Asp Cys Glu Arg Arg Phe
            420                 425                 430 agc aga tcc gac cag ctg aag aga cac cag cgg cac aca ggc gtg         1344
Ser Arg Ser Asp Gln Leu Lys Arg His Gln Arg His Thr Gly Val
        435                 440                 445 aaa cct ttc cag tgc aag acc tgc cag cgg aag ttc tcc aga agc gac     1392
Lys Pro Phe Gln Cys Lys Thr Cys Gln Arg Lys Phe Ser Arg Ser Asp
    450                 455                 460 cac ctg aaa acc cac acc cgg acc cac acc ggc aag acc tcc gag aag     1440
His Leu Lys Thr His Thr Arg Thr His Thr Gly Lys Thr Ser Glu Lys
465                 470                 475                 480 cca ttc agc tgc cgg tgg ccc agc tgc cag aag aag ttt gcc aga tct     1488
Pro Phe Ser Cys Arg Trp Pro Ser Cys Gln Lys Lys Phe Ala Arg Ser
                485                 490                 495 gac gag ctc gtg cgg cac cac aac atg cac cag cgg aac atg acc aaa     1536
Asp Glu Leu Val Arg His His Asn Met His Gln Arg Asn Met Thr Lys
            500                 505                 510 ctg cag ctg gct ctc tga                                             1554
Leu Gln Leu Ala Leu
        515
```

<210> SEQ ID NO 2
<211> LENGTH: 517
<212> TYPE: PRT
<213> ORGANISM: Artificial Sequence
<220> FEATURE:
<223> OTHER INFORMATION: Synthetic Construct

<400> SEQUENCE: 2

```
Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
```

```
                35                  40                  45
Ser Ala Glu Arg Leu Gln Gly Arg Arg Ser Arg Gly Ala Ser Gly Ser
 50                  55                  60
Glu Pro Gln Gln Met Gly Ser Asp Val Arg Asp Leu Asn Ala Leu Leu
65                  70                  75                  80
Pro Ala Val Pro Ser Leu Gly Gly Gly Gly Cys Ala Leu Pro Val
                85                  90                  95
Ser Gly Ala Ala Gln Trp Ala Pro Val Leu Asp Phe Ala Pro Pro Gly
                100                 105                 110
Ala Ser Ala Tyr Gly Ser Leu Gly Gly Pro Ala Pro Pro Pro Ala Pro
                115                 120                 125
Pro Pro Pro Pro Pro Pro Pro His Ser Phe Ile Lys Gln Glu Pro
    130                 135                 140
Ser Trp Gly Gly Ala Glu Pro His Glu Glu Gln Cys Leu Ser Ala Phe
145                 150                 155                 160
Thr Val His Phe Ser Gly Gln Phe Thr Gly Thr Ala Gly Ala Cys Arg
                165                 170                 175
Tyr Gly Pro Phe Gly Pro Pro Pro Ser Gln Ala Ser Ser Gly Gln
                180                 185                 190
Ala Arg Met Phe Pro Asn Ala Pro Tyr Leu Pro Ser Cys Leu Glu Ser
                195                 200                 205
Gln Pro Ala Ile Arg Asn Gln Gly Tyr Ser Thr Val Thr Phe Asp Gly
    210                 215                 220
Thr Pro Ser Tyr Gly His Thr Pro Ser His His Ala Ala Gln Phe Pro
225                 230                 235                 240
Asn His Ser Phe Lys His Glu Asp Pro Met Gly Gln Gln Gly Ser Leu
                245                 250                 255
Gly Glu Gln Gln Tyr Ser Val Pro Pro Val Tyr Gly Cys His Thr
                260                 265                 270
Pro Thr Asp Ser Cys Thr Gly Ser Gln Ala Leu Leu Leu Arg Thr Pro
    275                 280                 285
Tyr Ser Ser Asp Asn Leu Tyr Gln Met Thr Ser Gln Leu Glu Cys Met
    290                 295                 300
Thr Trp Asn Gln Met Asn Leu Gly Ala Thr Leu Lys Gly Val Ala Ala
305                 310                 315                 320
Gly Ser Ser Ser Ser Val Lys Trp Thr Glu Gly Gln Ser Asn His Ser
                325                 330                 335
Thr Gly Tyr Glu Ser Asp Asn His Thr Thr Pro Ile Leu Cys Gly Ala
                340                 345                 350
Gln Tyr Arg Ile His Thr His Gly Val Phe Arg Gly Ile Gln Asp Val
    355                 360                 365
Arg Arg Val Pro Gly Val Ala Pro Thr Leu Val Arg Ser Ala Ser Glu
370                 375                 380
Thr Ser Glu Lys Arg Pro Phe Met Cys Ala Tyr Pro Gly Cys Asn Lys
385                 390                 395                 400
Arg Tyr Phe Lys Leu Ser His Leu Gln Met His Ser Arg Lys His Thr
                405                 410                 415
Gly Glu Lys Pro Tyr Gln Cys Asp Phe Lys Asp Cys Glu Arg Arg Phe
                420                 425                 430
Ser Arg Ser Asp Gln Leu Lys Arg His Gln Arg Arg His Thr Gly Val
    435                 440                 445
Lys Pro Phe Gln Cys Lys Thr Cys Gln Arg Lys Phe Ser Arg Ser Asp
    450                 455                 460
```

```
His Leu Lys Thr His Thr Arg Thr His Thr Gly Lys Thr Ser Glu Lys
465                 470                 475                 480

Pro Phe Ser Cys Arg Trp Pro Ser Cys Gln Lys Lys Phe Ala Arg Ser
                485                 490                 495

Asp Glu Leu Val Arg His His Asn Met His Gln Arg Asn Met Thr Lys
            500                 505                 510

Leu Gln Leu Ala Leu
        515

<210> SEQ ID NO 3
<211> LENGTH: 1008
<212> TYPE: DNA
<213> ORGANISM: Artificial Sequence
<220> FEATURE:
<223> OTHER INFORMATION: Synthetic nucleic acid encoding human CD1d
<220> FEATURE:
<221> NAME/KEY: CDS
<222> LOCATION: (1)..(1008)

<400> SEQUENCE: 3
```

| | | | | | | | | | | | | | | | | |
|---|---|---|---|---|---|---|---|---|---|---|---|---|---|---|---|---|
| atg | ggc | tgc | ctg | ctg | ttt | ctg | ctg | ctg | tgg | gcc | ctg | ctg | cag | gcc | tgg | 48 |
| Met | Gly | Cys | Leu | Leu | Phe | Leu | Leu | Leu | Trp | Ala | Leu | Leu | Gln | Ala | Trp | |
| 1 | | | | 5 | | | | | 10 | | | | | 15 | | |
| gga | tct | gct | gaa | gtg | ccc | cag | aga | ctg | ttc | ccc | ctg | cgg | tgc | ctg | cag | 96 |
| Gly | Ser | Ala | Glu | Val | Pro | Gln | Arg | Leu | Phe | Pro | Leu | Arg | Cys | Leu | Gln | |
| | | | 20 | | | | | 25 | | | | | 30 | | | |
| atc | agc | agc | ttc | gcc | aac | agc | agc | tgg | acc | aga | acc | gat | ggc | ctg | gcc | 144 |
| Ile | Ser | Ser | Phe | Ala | Asn | Ser | Ser | Trp | Thr | Arg | Thr | Asp | Gly | Leu | Ala | |
| | | 35 | | | | | 40 | | | | | 45 | | | | |
| tgg | ctg | gga | gag | ctg | cag | aca | cac | agc | tgg | tcc | aac | gac | agc | gac | acc | 192 |
| Trp | Leu | Gly | Glu | Leu | Gln | Thr | His | Ser | Trp | Ser | Asn | Asp | Ser | Asp | Thr | |
| 50 | | | | | 55 | | | | | 60 | | | | | | |
| gtg | cgg | agc | ctg | aag | cct | tgg | agc | cag | ggc | acc | ttt | agc | gac | cag | cag | 240 |
| Val | Arg | Ser | Leu | Lys | Pro | Trp | Ser | Gln | Gly | Thr | Phe | Ser | Asp | Gln | Gln | |
| 65 | | | | 70 | | | | | 75 | | | | | 80 | | |
| tgg | gag | aca | ctg | cag | cac | atc | ttc | cgg | gtg | tac | aga | agc | agc | ttc | acc | 288 |
| Trp | Glu | Thr | Leu | Gln | His | Ile | Phe | Arg | Val | Tyr | Arg | Ser | Ser | Phe | Thr | |
| | | | | 85 | | | | | 90 | | | | | 95 | | |
| cgg | gac | gtg | aaa | gaa | ttt | gcc | aag | atg | ctg | cgg | ctg | agc | tac | ccc | ctg | 336 |
| Arg | Asp | Val | Lys | Glu | Phe | Ala | Lys | Met | Leu | Arg | Leu | Ser | Tyr | Pro | Leu | |
| | | | 100 | | | | | 105 | | | | | 110 | | | |
| gaa | ctg | cag | gtg | tcc | gcc | ggc | tgt | gaa | gtg | cac | cct | ggc | aac | gcc | agc | 384 |
| Glu | Leu | Gln | Val | Ser | Ala | Gly | Cys | Glu | Val | His | Pro | Gly | Asn | Ala | Ser | |
| | | 115 | | | | | 120 | | | | | 125 | | | | |
| aac | aac | ttc | ttc | cac | gtg | gcc | ttc | cag | ggc | aag | gac | ata | ctg | agc | ttt | 432 |
| Asn | Asn | Phe | Phe | His | Val | Ala | Phe | Gln | Gly | Lys | Asp | Ile | Leu | Ser | Phe | |
| | 130 | | | | | 135 | | | | | 140 | | | | | |
| cag | ggc | acc | agc | tgg | gag | ccc | aca | cag | gaa | gct | cca | ctg | tgg | gtc | aac | 480 |
| Gln | Gly | Thr | Ser | Trp | Glu | Pro | Thr | Gln | Glu | Ala | Pro | Leu | Trp | Val | Asn | |
| 145 | | | | | 150 | | | | | 155 | | | | | 160 | |
| ctg | gcc | atc | cag | gtg | ctg | aac | cag | gac | aag | tgg | acc | cgg | gaa | acc | gtg | 528 |
| Leu | Ala | Ile | Gln | Val | Leu | Asn | Gln | Asp | Lys | Trp | Thr | Arg | Glu | Thr | Val | |
| | | | | 165 | | | | | 170 | | | | | 175 | | |
| cag | tgg | ctg | ctg | aac | ggc | acc | tgt | ccc | cag | ttt | gtg | tcc | ggc | ctg | ctg | 576 |
| Gln | Trp | Leu | Leu | Asn | Gly | Thr | Cys | Pro | Gln | Phe | Val | Ser | Gly | Leu | Leu | |
| | | | 180 | | | | | 185 | | | | | 190 | | | |
| gaa | agc | ggc | aag | agc | gag | ctg | aag | aaa | caa | gtg | aag | ccc | aaa | gcc | tgg | 624 |
| Glu | Ser | Gly | Lys | Ser | Glu | Leu | Lys | Lys | Gln | Val | Lys | Pro | Lys | Ala | Trp | |
| | | 195 | | | | | 200 | | | | | 205 | | | | |
| ctg | agc | aga | ggc | cct | tct | cct | gga | cct | gga | cgg | ctg | ctg | ctc | gtg | tgt | 672 |

-continued

```
Leu Ser Arg Gly Pro Ser Pro Gly Pro Gly Arg Leu Leu Val Cys
    210             215             220 cac gtg tcc ggc ttc tac ccc aag ccc gtg tgg gtc aag tgg atg cgg      720
His Val Ser Gly Phe Tyr Pro Lys Pro Val Trp Val Lys Trp Met Arg
225             230             235             240 gga gaa cag gaa cag cag ggc acc cag cct ggc gac atc ctg cct aac      768
Gly Glu Gln Glu Gln Gln Gly Thr Gln Pro Gly Asp Ile Leu Pro Asn
                245             250             255 gcc gac gag aca tgg tat ctg cgg gcc acc ctg gat gtg gtg gct ggc      816
Ala Asp Glu Thr Trp Tyr Leu Arg Ala Thr Leu Asp Val Val Ala Gly
            260             265             270 gaa gca gcc ggc ctg tcc tgt aga gtg aag cac agc agc ctg gaa gga      864
Glu Ala Ala Gly Leu Ser Cys Arg Val Lys His Ser Ser Leu Glu Gly
        275             280             285 cag gac atc gtg ctg tac tgg ggc ggc agc tac acc agc atg gga ctg      912
Gln Asp Ile Val Leu Tyr Trp Gly Gly Ser Tyr Thr Ser Met Gly Leu
    290             295             300 att gct ctg gcc gtg ctg gcc tgt ctg ctg ttt ctg ctg atc gtg gga      960
Ile Ala Leu Ala Val Leu Ala Cys Leu Leu Phe Leu Leu Ile Val Gly
305             310             315             320 ttc acc agc cgg ttc aag cgg cag acc agc tac cag ggc gtg ctc tga     1008
Phe Thr Ser Arg Phe Lys Arg Gln Thr Ser Tyr Gln Gly Val Leu
                325             330             335

<210> SEQ ID NO 4
<211> LENGTH: 335
<212> TYPE: PRT
<213> ORGANISM: Artificial Sequence
<220> FEATURE:
<223> OTHER INFORMATION: Synthetic Construct

<400> SEQUENCE: 4

Met Gly Cys Leu Leu Phe Leu Leu Leu Trp Ala Leu Leu Gln Ala Trp
1               5                   10                  15

Gly Ser Ala Glu Val Pro Gln Arg Leu Phe Pro Leu Arg Cys Leu Gln
            20                  25                  30

Ile Ser Ser Phe Ala Asn Ser Ser Trp Thr Arg Thr Asp Gly Leu Ala
        35                  40                  45

Trp Leu Gly Glu Leu Gln Thr His Ser Trp Ser Asn Asp Ser Asp Thr
    50                  55                  60

Val Arg Ser Leu Lys Pro Trp Ser Gln Gly Thr Phe Ser Asp Gln Gln
65                  70                  75                  80

Trp Glu Thr Leu Gln His Ile Phe Arg Val Tyr Arg Ser Ser Phe Thr
                85                  90                  95

Arg Asp Val Lys Glu Phe Ala Lys Met Leu Arg Leu Ser Tyr Pro Leu
            100                 105                 110

Glu Leu Gln Val Ser Ala Gly Cys Glu Val His Pro Gly Asn Ala Ser
        115                 120                 125

Asn Asn Phe Phe His Val Ala Phe Gln Gly Lys Asp Ile Leu Ser Phe
    130                 135                 140

Gln Gly Thr Ser Trp Glu Pro Thr Gln Glu Ala Pro Leu Trp Val Asn
145                 150                 155                 160

Leu Ala Ile Gln Val Leu Asn Gln Asp Lys Trp Thr Arg Glu Thr Val
                165                 170                 175

Gln Trp Leu Leu Asn Gly Thr Cys Pro Gln Phe Val Ser Gly Leu Leu
            180                 185                 190

Glu Ser Gly Lys Ser Glu Leu Lys Lys Gln Val Lys Pro Lys Ala Trp
        195                 200                 205
```

```
Leu Ser Arg Gly Pro Ser Pro Gly Pro Gly Arg Leu Leu Val Cys
        210                 215                 220

His Val Ser Gly Phe Tyr Pro Lys Pro Val Trp Val Lys Trp Met Arg
225                 230                 235                 240

Gly Glu Gln Glu Gln Gln Gly Thr Gln Pro Gly Asp Ile Leu Pro Asn
                245                 250                 255

Ala Asp Glu Thr Trp Tyr Leu Arg Ala Thr Leu Asp Val Val Ala Gly
                260                 265                 270

Glu Ala Ala Gly Leu Ser Cys Arg Val Lys His Ser Ser Leu Glu Gly
                275                 280                 285

Gln Asp Ile Val Leu Tyr Trp Gly Gly Ser Tyr Thr Ser Met Gly Leu
                290                 295                 300

Ile Ala Leu Ala Val Leu Ala Cys Leu Leu Phe Leu Leu Ile Val Gly
305                 310                 315                 320

Phe Thr Ser Arg Phe Lys Arg Gln Thr Ser Tyr Gln Gly Val Leu
                325                 330                 335

<210> SEQ ID NO 5
<211> LENGTH: 1011
<212> TYPE: DNA
<213> ORGANISM: Artificial Sequence
<220> FEATURE:
<223> OTHER INFORMATION: Synthetic nucleic acid encoding mouse CD1d
<220> FEATURE:
<221> NAME/KEY: CDS
<222> LOCATION: (1)..(1011)

<400> SEQUENCE: 5 atg aga tac ctg ccc tgg ctg ctg ctg tgg gcc ttc ctc cag gtg tgg     48
Met Arg Tyr Leu Pro Trp Leu Leu Leu Trp Ala Phe Leu Gln Val Trp
1               5                   10                  15 gga cag tct gag gcc cag cag aag aac tac acc ttc cgg tgc ctg cag     96
Gly Gln Ser Glu Ala Gln Gln Lys Asn Tyr Thr Phe Arg Cys Leu Gln
            20                  25                  30 atg agc agc ttc gcc aac aga agc tgg tcc cgg acc gac agc gtc gtg    144
Met Ser Ser Phe Ala Asn Arg Ser Trp Ser Arg Thr Asp Ser Val Val
        35                  40                  45 tgg ctg gga gat ctg cag acc cac aga tgg tcc aac gac agc gcc acc    192
Trp Leu Gly Asp Leu Gln Thr His Arg Trp Ser Asn Asp Ser Ala Thr
    50                  55                  60 atc agc ttc acc aag ccc tgg tcc cag ggc aag ctg agc aac cag cag    240
Ile Ser Phe Thr Lys Pro Trp Ser Gln Gly Lys Leu Ser Asn Gln Gln
65                  70                  75                  80 tgg gag aag ctg cag cac atg ttc cag gtg tac cgg gtg tcc ttc acc    288
Trp Glu Lys Leu Gln His Met Phe Gln Val Tyr Arg Val Ser Phe Thr
                85                  90                  95 cgg gac atc cag gaa ctc gtg aag atg atg agc ccc aaa gag gac tac    336
Arg Asp Ile Gln Glu Leu Val Lys Met Met Ser Pro Lys Glu Asp Tyr
            100                 105                 110 ccc atc gag atc cag ctg agc gcc ggc tgc gag atg tac cct ggc aat    384
Pro Ile Glu Ile Gln Leu Ser Ala Gly Cys Glu Met Tyr Pro Gly Asn
        115                 120                 125 gcc agc gag agc ttc ctg cac gtg gcc ttc cag ggc aaa tac gtc gtg    432
Ala Ser Glu Ser Phe Leu His Val Ala Phe Gln Gly Lys Tyr Val Val
    130                 135                 140 cgg ttc tgg ggc acc agc tgg cag aca gtg cct ggc gct cct agc tgg    480
Arg Phe Trp Gly Thr Ser Trp Gln Thr Val Pro Gly Ala Pro Ser Trp
145                 150                 155                 160 ctg gac ctg cct atc aag gtg ctg aac gcc gac cag ggc aca agc gcc    528
```

```
Leu Asp Leu Pro Ile Lys Val Leu Asn Ala Asp Gln Gly Thr Ser Ala
            165                 170                 175 aca gtg cag atg ctg ctg aac gac aca tgc ccc ctg ttc gtg cgg gga    576
Thr Val Gln Met Leu Leu Asn Asp Thr Cys Pro Leu Phe Val Arg Gly
        180                 185                 190 ctg ctg gaa gcc ggc aag agc gac ctg gaa aag cag gaa aag ccc gtg    624
Leu Leu Glu Ala Gly Lys Ser Asp Leu Glu Lys Gln Glu Lys Pro Val
            195                 200                 205 gcc tgg ctg agc agc gtg cca tct tct gcc gat ggc cac aga cag ctc    672
Ala Trp Leu Ser Ser Val Pro Ser Ser Ala Asp Gly His Arg Gln Leu
    210                 215                 220 gtg tgc cac gtg tcc ggc ttc tac ccc aag ccc gtg tgg gtc atg tgg    720
Val Cys His Val Ser Gly Phe Tyr Pro Lys Pro Val Trp Val Met Trp
225                 230                 235                 240 atg cgg ggc gac cag gaa cag cag ggc aca cac aga ggc gac ttt ctg    768
Met Arg Gly Asp Gln Glu Gln Gln Gly Thr His Arg Gly Asp Phe Leu
                245                 250                 255 ccc aac gcc gac gag aca tgg tat ctg caa gcc acc ctg gac gtg gaa    816
Pro Asn Ala Asp Glu Thr Trp Tyr Leu Gln Ala Thr Leu Asp Val Glu
            260                 265                 270 gct ggc gag gaa gct gga ctg gcc tgc aga gtg aag cac agc tct ctg    864
Ala Gly Glu Glu Ala Gly Leu Ala Cys Arg Val Lys His Ser Ser Leu
        275                 280                 285 ggc ggc cag gac atc atc ctg tac tgg gat gcc aga cag gcc cca gtg    912
Gly Gly Gln Asp Ile Ile Leu Tyr Trp Asp Ala Arg Gln Ala Pro Val
    290                 295                 300 ggc ctg atc gtg ttc atc gtg ctg atc atg ctg gtg gtc gtg ggc gcc    960
Gly Leu Ile Val Phe Ile Val Leu Ile Met Leu Val Val Val Gly Ala
305                 310                 315                 320 gtg gtg tac tac atc tgg cgg aga aga agc gcc tac cag gat atc aga   1008
Val Val Tyr Tyr Ile Trp Arg Arg Arg Ser Ala Tyr Gln Asp Ile Arg
                325                 330                 335 tga                                                               1011

<210> SEQ ID NO 6
<211> LENGTH: 336
<212> TYPE: PRT
<213> ORGANISM: Artificial Sequence
<220> FEATURE:
<223> OTHER INFORMATION: Synthetic Construct

<400> SEQUENCE: 6

Met Arg Tyr Leu Pro Trp Leu Leu Leu Trp Ala Phe Leu Gln Val Trp
1               5                   10                  15

Gly Gln Ser Glu Ala Gln Gln Lys Asn Tyr Thr Phe Arg Cys Leu Gln
            20                  25                  30

Met Ser Ser Phe Ala Asn Arg Ser Trp Ser Arg Thr Asp Ser Val Val
        35                  40                  45

Trp Leu Gly Asp Leu Gln Thr His Arg Trp Ser Asn Asp Ser Ala Thr
    50                  55                  60

Ile Ser Phe Thr Lys Pro Trp Ser Gln Gly Lys Leu Ser Asn Gln Gln
65                  70                  75                  80

Trp Glu Lys Leu Gln His Met Phe Gln Val Tyr Arg Val Ser Phe Thr
                85                  90                  95

Arg Asp Ile Gln Glu Leu Val Lys Met Met Ser Pro Lys Glu Asp Tyr
            100                 105                 110

Pro Ile Glu Ile Gln Leu Ser Ala Gly Cys Glu Met Tyr Pro Gly Asn
        115                 120                 125
```

-continued

```
Ala Ser Glu Ser Phe Leu His Val Ala Phe Gln Gly Lys Tyr Val Val
    130                 135                 140
Arg Phe Trp Gly Thr Ser Trp Gln Thr Val Pro Gly Ala Pro Ser Trp
145                 150                 155                 160
Leu Asp Leu Pro Ile Lys Val Leu Asn Ala Asp Gln Gly Thr Ser Ala
                165                 170                 175
Thr Val Gln Met Leu Leu Asn Asp Thr Cys Pro Leu Phe Val Arg Gly
                180                 185                 190
Leu Leu Glu Ala Gly Lys Ser Asp Leu Glu Lys Gln Glu Lys Pro Val
            195                 200                 205
Ala Trp Leu Ser Ser Val Pro Ser Ser Ala Asp Gly His Arg Gln Leu
    210                 215                 220
Val Cys His Val Ser Gly Phe Tyr Pro Lys Pro Val Trp Val Met Trp
225                 230                 235                 240
Met Arg Gly Asp Gln Glu Gln Gln Gly Thr His Arg Gly Asp Phe Leu
                245                 250                 255
Pro Asn Ala Asp Glu Thr Trp Tyr Leu Gln Ala Thr Leu Asp Val Glu
                260                 265                 270
Ala Gly Glu Glu Ala Gly Leu Ala Cys Arg Val Lys His Ser Ser Leu
            275                 280                 285
Gly Gly Gln Asp Ile Ile Leu Tyr Trp Asp Ala Arg Gln Ala Pro Val
    290                 295                 300
Gly Leu Ile Val Phe Ile Val Leu Ile Met Leu Val Val Val Gly Ala
305                 310                 315                 320
Val Val Tyr Tyr Ile Trp Arg Arg Arg Ser Ala Tyr Gln Asp Ile Arg
                325                 330                 335
```

METHOD FOR TREATING CANCER USING ARTIFICIAL ADJUVANT CELL (AAVC)

CROSS-REFERENCE TO RELATED APPLICATIONS

This application is the U.S. National Stage of PCT/JP2020/044587, filed Dec. 1, 2020, which claims priority to JP 2019-217712, filed Dec. 2, 2019.

The instant application contains a Sequence Listing which has been submitted in ASCII format via EFS-WEB and is hereby incorporated by reference in its entirety. Said ASCII copy, created on Jun. 7, 2021, is named sequence.txt and is 28,526 bytes.

TECHNICAL FIELD

The present invention relates to an effective and safe method for treating or preventing a cancer using an artificial adjuvant cell (aAVC).

BACKGROUND ART

Natural killer T (NKT) cells are immune cells having the features of T cells and natural killer (NK) cells, and are activated by a CD1d ligand composed of glycolipid loaded on a major histocompatibility complex (MHC)-like molecule CD1d on antigen presenting cells (APC). The activated NKT cells are known to induce enhancement in direct cytotoxicity mediated by perforin/granzyme B, etc. as well as to produce cytokines such as interferon gamma (IFN-γ) or interleukin-4 (IL-4), thereby inducing the differentiation and proliferation of the NKT cells themselves and activating T cells, NK cells and B cells.

CD1d ligands capable of activating NKT cells include, for example, α-galactosylceramide (α-GalCer), α-C-galactosylceramide (α-C-GalCer), 7DW8-5, and isoglobotrihexosylceramide (iGb3). Known CD1d-expressing APCs include, for example, macrophages, dendritic cells (DC), B cells, and B cell lymphocytic leukemia (B-CLL) cells.

NKT cells activated by DC pulsed with α-GalCer exhibit cytotoxicity to various cancer cells. It has been reported that DC pulsed with α-GalCer more strongly induces IFN-γ-producing NKT cells and exhibits a high antitumor effect, as compared with administration of free α-GalCer (Non Patent Literatures 1 and 2). Clinical trials have also been conducted targeting lung cancer patients (Non Patent Literatures 3 and 4).

It has been reported that in mouse models, the administration of α-GalCer induces an antitumor effect by the activation of innate immunity via NKT cell activation, whereas adverse effects such as hepatocyte necrosis are manifested due to the production of inflammatory cytokines associated with the activation of NKT cells, etc. (Non Patent Literature 5). Furthermore, in clinical trials of α-GalCer, the administration of α-GalCer has induced immune response leading to an antitumor effect, and on the other hand, has been found to cause adverse events showing deterioration of general conditions, such as headache, vomiting, chills, and a feeling of malaise, indicating the possibility of inducing various adverse reactions (Non Patent Literature 6).

Fujii et al. have prepared aAVC by causing human-derived cells to exogenously express CD1d and a cancer antigen, and further pulsing the cells with α-GalCer (Patent Literatures 1 to 3). This aAVC activates NKT cells via its CD1d/α-GalCer complex, and the activated NKT cells produce cytokines such as IFN-γ, which activates NK cells or the like. In mouse models, the administration of aAVC has been shown to have an NK cell-dependent antitumor effect (Patent Literatures 1 to 3 and Non Patent Literatures 7 and 8). aAVC administered to mice is immediately killed by activated NKT cells in vivo, and fragments of the aAVC are taken up into dendritic cells. The dendritic cells with the aAVC fragment thus taken up present the cancer antigen incorporated in MHC on the cell surface, and induce cancer antigen-specific T cells. In mouse models, the administration of aAVC has also been shown to have an antitumor effect via the induction of cancer antigen-specific T cells (Patent Literatures 1 to 3 and Non Patent Literatures 7 and 8). Thus, aAVC has been shown to be capable of strongly inducing two immune mechanisms, i.e., innate immunity activation shown by NK cell activation mediated by NKT cell activation and induction of adaptive immunity shown by induction of antigen-specific T cells. However, no study has yet been conducted to determine a proper clinical dose of aAVC that exerts an antitumor effect by innate immunity activation and can be safely used.

CITATION LIST

Patent Literature

[Patent Literature 1] International Publication No. WO 2007/097370
[Patent Literature 2] International Publication No. WO 2010/061930
[Patent Literature 3] International Publication No. WO

Non Patent Literature

[Non Patent Literature 1] "The Journal of Immunology", (USA), 1999; 163 (5): 2387-2391
[Non Patent Literature 2] "Nature Immunology", (USA), 2002; 3 (9): 867-874
[Non Patent Literature 3] "The Journal of Immunology", (USA), 2009; 182 (4): 2492-2501
[Non Patent Literature 4] "Clinical Cancer Research", (USA), 2005; 11 (5): 1910-1917
[Non Patent Literature 5] "Anticancer Research", 2016; 36 (7): 3667-3672
[Non Patent Literature 6] "Clinical Cancer Research", (USA), 2002; 8 (12): 3702-3709
[Non Patent Literature 7] "Cancer Research", (USA), 2013; 73 (1): 62-73
[Non Patent Literature 8] "Cancer Research", (USA), 2016; 76 (13): 3756-3766

SUMMARY OF INVENTION

Technical Problem

An object of the present invention is to provide an effective and safe method for treating or preventing a cancer using aAVC.

Solution to Problem

The present inventors have conducted diligent studies on the clinical application of aAVC. The present inventors have found that the amount of α-GalCer loaded on aAVC in the course of aAVC manufacturing processes varies depending on the type of cells and conditions for pulsing cells with α-GalCer, etc. The need of standardizing the amount of α-GalCer loaded on aAVC has thereby been found in order to produce aAVC as medicaments. Accordingly, the present inventors have established a method for measuring the amount of α-GalCer loaded on cell surface in order to quantify the amount of α-GalCer loaded on aAVC. The present inventors have further confirmed that adding various concentrations of α-GalCer into the medium when pulsing aAVC with α-GalCer results in variations in the amount of α-GalCer loaded on the cell (Example 2). The present inventors have further found that the dose of α-GalCer loaded on aAVC is related to the induction of an antitumor effect and adverse reactions attributable to innate immunity activation mediated by NKT cells (Examples 3 to 5). In this way, the present inventors have successfully found the dose of α-GalCer loaded on aAVC, and the amount of α-GalCer loaded on aAVC in a pharmaceutical composition comprising aAVC, which are preferred in terms of effectiveness and safety in the treatment and prevention of a cancer using aAVC. Specifically, the present invention provides an effective and safe method for treating or preventing a cancer using aAVC, aAVC for effective and safe treatment or prevention of a cancer, and a pharmaceutical composition comprising the same, etc.

Specifically, the present invention may include the following aspects as a medically or industrially useful substance or method.

[1] A method for treating or preventing a cancer, comprising the step of administering a human-derived cell to a human, wherein the cell expresses exogenous CD1d, and has α-GalCer loaded on the cell surface,
and wherein the cell is administered to the human such that a single dose of α-GalCer loaded on the cell surface ranges from 1.7 ng to 275 ng per kg body weight of the human.
[2] The method according to [1], wherein the human-derived cell expresses an exogenous cancer antigen.
[3] The method according to [1] or [2], wherein the CD1d is human CD1d.
[4] The method according to any of [1] to [3], wherein the human-derived cell is a human embryonic kidney cell 293 (HEK293)-derived cell.
[5] The method according to any of [1] to [4], wherein the amount of α-GalCer loaded on the cell surface is in the range of 3.9 to 275 ng per $1 \times 10^6$ cells.
[6] A pharmaceutical composition for treating or preventing a cancer, comprising a human-derived cell, wherein the cell expresses exogenous CD1d and has α-GalCer loaded on the cell surface,
and wherein the composition is administered to a human such that a single dose of α-GalCer loaded on the cell surface ranges from 1.7 ng to 275 ng per kg body weight of the human.
[7] The pharmaceutical composition according to [6], wherein the human-derived cell expresses an exogenous cancer antigen.
[8] The pharmaceutical composition according to [6] or [7], wherein the CD1d is human CD1d.
[9] The pharmaceutical composition according to any of [6] to [8], wherein the human-derived cell is a human embryonic kidney cell 293 (HEK293)-derived cell.
[10] The pharmaceutical composition according to any of [6] to [9], wherein the amount of α-GalCer loaded on the cell surface is in the range of 3.9 to 275 ng per $1 \times 10^6$ cells.
[11] Use of a human-derived cell for producing a pharmaceutical composition for treating or preventing a cancer, wherein the cell expresses exogenous CD1d and has α-GalCer loaded on the cell surface,
and wherein the composition is administered to a human such that a single dose of α-GalCer loaded on the cell surface ranges from 1.7 ng to 275 ng per kg body weight of the human.
[12] The use according to [11], wherein the human-derived cell expresses an exogenous cancer antigen.
[13] The use according to [11] or [12], wherein the CD1d is human CD1d.
[14] The use according to any of [11] to [13], wherein the human-derived cell is a human embryonic kidney cell 293 (HEK293)-derived cell.
[15] The use according to any of [11] to [14], wherein the amount of α-GalCer loaded on the cell surface is in the range of 3.9 to 275 ng per $1 \times 10^6$ cells.
[16] A human-derived cell for use in treating or preventing a cancer,
wherein the cell expresses exogenous CD1d and has α-GalCer loaded on the cell surface,
and wherein the cell is administered to a human such that a single dose of α-GalCer loaded on the cell surface ranges from 1.7 ng to 275 ng per kg body weight of the human.
[17] The human-derived cell according to [16], wherein the human-derived cell expresses an exogenous cancer antigen.
[18] The human-derived cell according to [16] or [17], wherein the CD1d is human CD1d.
[19] The human-derived cell according to any of [16] to [18], wherein the human-derived cell is a human embryonic kidney cell 293 (HEK293)-derived cell.
[20] The human-derived cell according to any of [16] to [19], wherein the amount of α-GalCer loaded on the cell surface is in the range of 3.9 to 275 ng per $1 \times 10^6$ cells.
[21] A method for producing a human-derived cell that expresses exogenous CD1d and has α-GalCer loaded on the cell surface, wherein the cell is administered to a human such that a single dose of α-GalCer loaded on the cell surface ranges from 1.7 ng to 275 ng per kg body weight of the human, and wherein the method comprises the step of culturing human-derived cells expressing exogenous CD1d in a culture medium containing 56 ng/mL to 3000 ng/mL α-GalCer.
[22] The method according to [21], further comprising the step of measuring the amount of α-GalCer loaded on the cells obtained by the culture step, and selecting a cell wherein the amount of α-GalCer loaded on the cell surface is in the range of 3.9 to 275 ng per $1 \times 10^6$ cells.

Advantageous Effects of Invention

The method of the present invention can be used for effectively and safely preventing or treating a cancer using aAVC.

Figure 2:
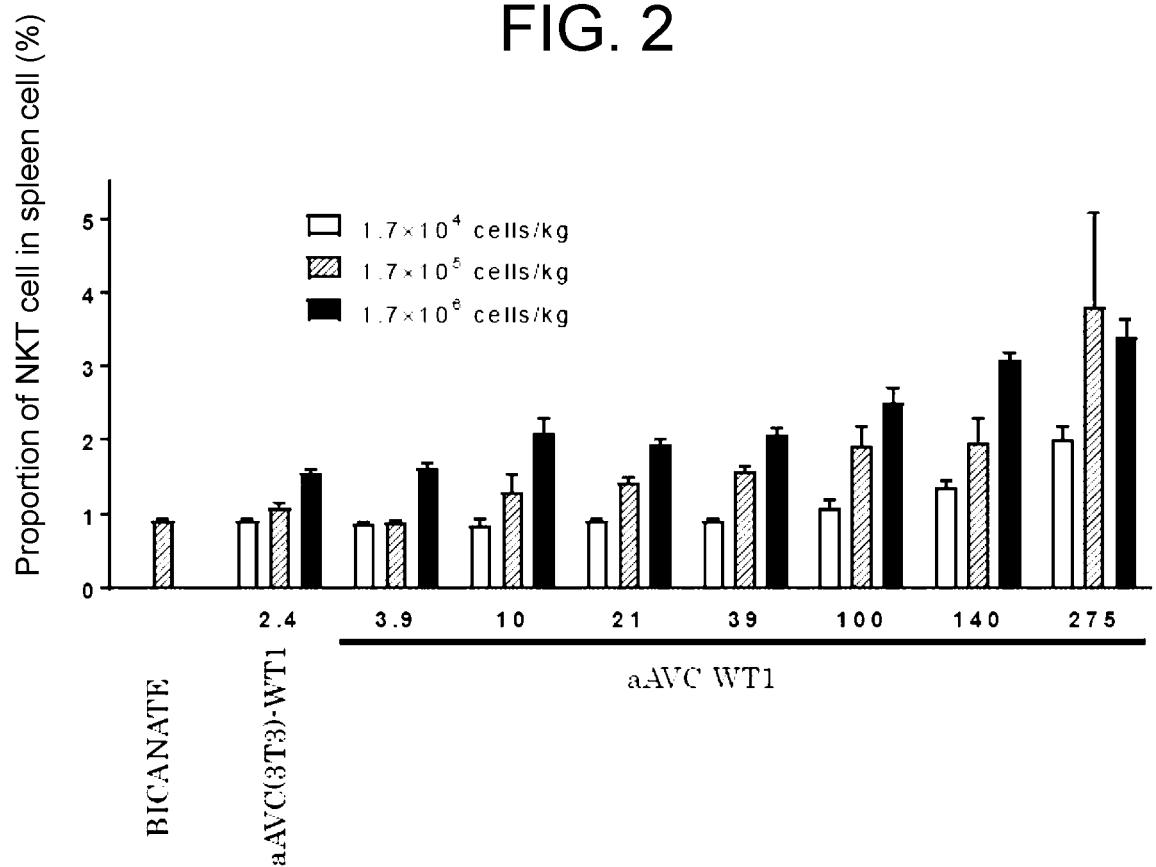

FIG. 2 shows the proportion (%) of NKT cells in spleen cells after administration of aAVC(3T3)-WT1 or each aAVC-WT1 described in Table 2. BICANATE or each dose of aAVC(3T3)-WT1 or aAVC-WT1 was administered to the tail vein of each 5-week-old C57BL/6J female mice (n=3 in each group). Three days after administration, the spleen was collected, and NKT cells were detected by flow cytometry. The proportion of NKT cells was defined as the proportion of CD1d/Gal-dimer-positive and CD19-negative cells in lymphocyte-fraction cells of a forward scatter and side scatter cytogram, and indicated by mean±standard error in the graph. The numeric values on the X-axis indicate the amount of α-GalCer loaded on aAVC (ng/$10^6$ cells).

Figure 3:
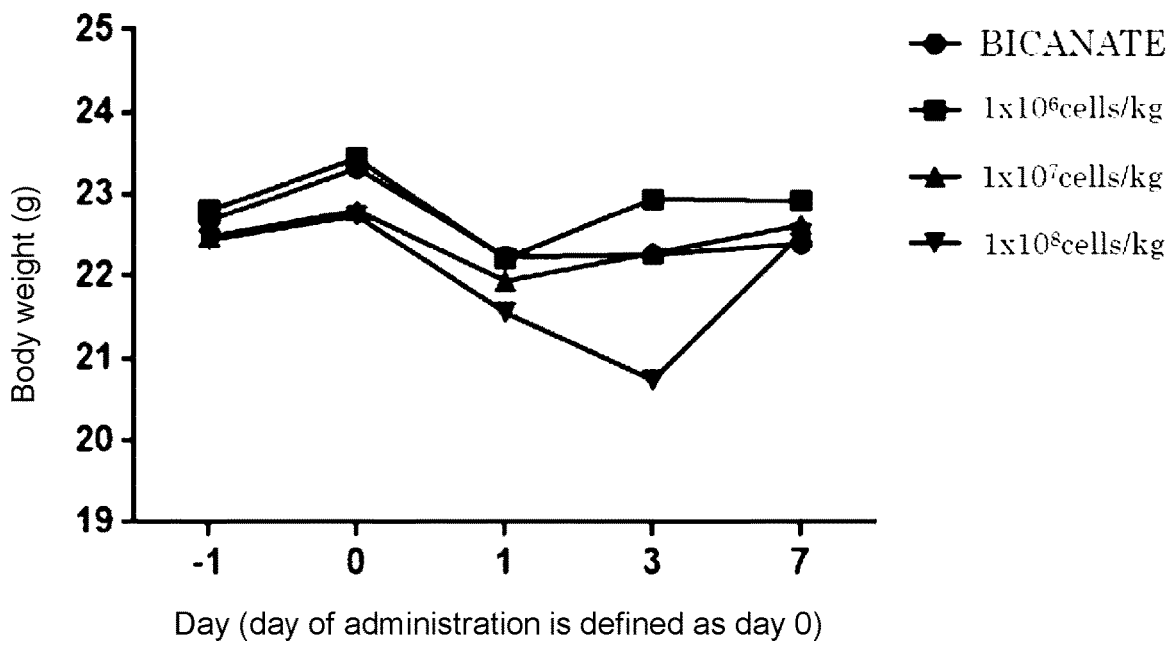
Figure 3:
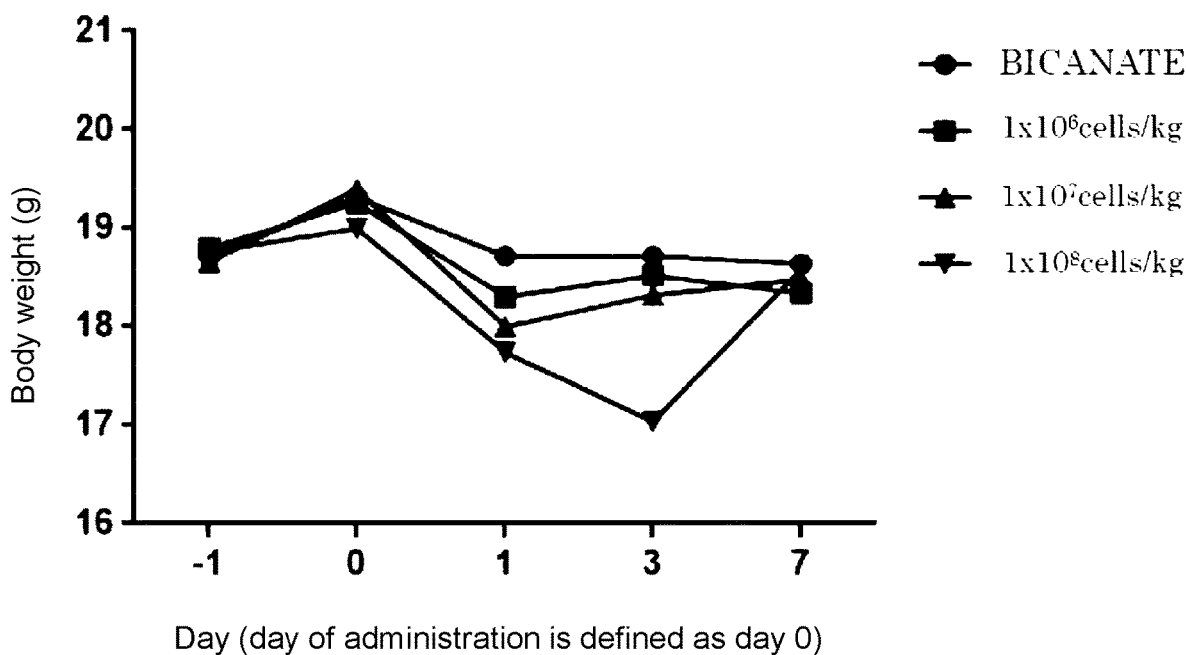

FIG. 3 shows results of measuring the body weights of male mice or female mice in a toxicity study after single-dose intravenous administration of aAVC-WT1 in mice. BICANATE or each dose of aAVC-WT1 was administered once to the tail vein of each 8-week-old female or male C57BL/6J mice (n=5 in each group). The body weights were measured on the day before administration (day −1), the day of administration (day 0), the day following administration (day 1), 3 days after administration (day 3) and 7 days after administration (day 7), and shown in a graph.

Figure 4:
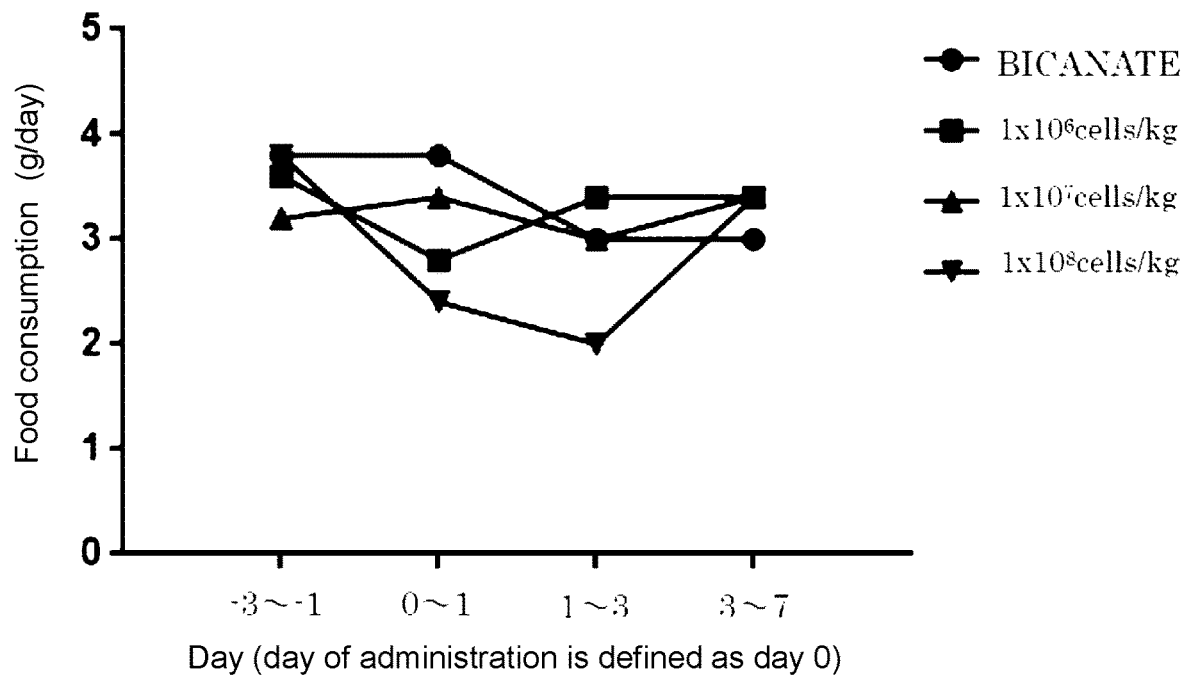
Figure 4:
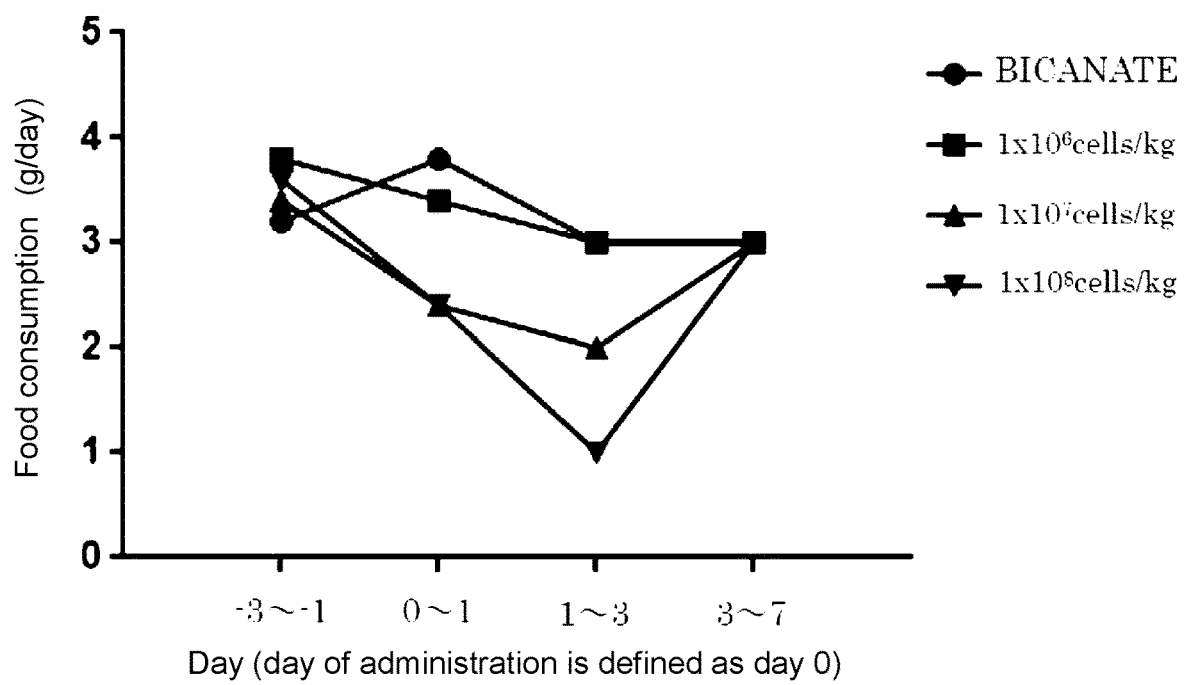

FIG. 4 shows results of measuring the food consumptions of male mice or female mice in a toxicity study for single-dose intravenous administration in mice. BICANATE or each dose of aAVC-WT1 was administered once to the tail vein of each 8-week-old female or male C57BL/6J mice (n=5 in each group). The food consumptions per day (g/day) were measured from 3 days before administration to the day before administration (days −3 to −1), from the day of administration to the day following administration (days 0 to 1), from the day following administration to 3 days after administration (days 1 to 3), and from 3 days after administration to 7 days after administration (days 3 to 7), and shown in a graph.

DESCRIPTION OF EMBODIMENTS

Hereinafter, the present invention will be described in detail. However, the present invention is not limited to the embodiments described below. Scientific terms and technical terms used in relation to the present invention have meanings generally understood by those skilled in the art, unless otherwise specified herein.

<Method for Treating or Preventing Cancer According to the Present Invention>

The present invention provides the following method for treating or preventing a cancer:

a method for treating or preventing a cancer, comprising the step of administering a human-derived cell to a human, wherein the cell expresses exogenous or endogenous CD1d, and has α-GalCer loaded on the cell surface,
and wherein the cell is administered to the human such that a single dose of α-GalCer loaded on the cell surface ranges from 1.7 ng to 275 ng per kg body weight of the human.

1. aAVC

The method of the present invention can employ a human-derived cell that expresses exogenous or endogenous CD1d, and has α-GalCer loaded on the cell surface (also referred to as aAVC in the present specification). aAVC may further express one or more exogenous or endogenous cancer antigen(s). Although, aAVC without expressing cancer antigens(s) can activates NKT cells and shows a certain degree of antitumor effect, aAVC expressing a cancer antigen(s) has/have more advantage to induce adaptive immunity against a cancer. aAVC can be easily prepared by those skilled in the art using a method known in the art (e.g., Non Patent Literatures 7 and 8 and Patent Literatures 1 to 3).

The human-derived cell used in the present invention can be a cell derived from an arbitrary human tissue of, for example, stomach, small intestine, large intestine, lung, pancreas, kidney, liver, thymus gland, spleen, prostate, ovary, uterus, bone marrow, skin, muscle, or peripheral blood. The human-derived cell used in the present invention may have an ability to proliferate. In one embodiment, the human-derived cell used in the present invention is a non-hemocyte cell. The human-derived cell used in the present invention can be a cell derived from a particular type of cell in a human tissue (e.g., epithelial cells, endothelial cells, epidermal cells, stromal cells, fibroblasts, adipocytes, mammary gland cells, mesangial cells, pancreatic β cells, nerve cells, glial cells, exocrine epithelial cells, endocrine cells, skeletal muscle cells, smooth muscle cells, myocardial cells, osteoblasts, embryonic cells, and immune cells). The human-derived cell used in the present invention may be a normal cell or a cancer cell. In one embodiment, the human-derived cell used in the present invention is a normal cell. In one embodiment, the human-derived cell used in the present invention can be a human embryonic kidney cell 293 (HEK293) cell (J. Gen. Virol.; 1977; 36: 59-74), a WI-38 cell, an SC-01MFP cell, and an MRC-5 cell, or a cell derived from any of these cells. In one embodiment, the human-derived cell used in the present invention is a HEK293-derived cell. In one embodiment, the human-derived cell used in the present invention is a FreeStyle™ 293-F cell.

In one embodiment, the human-derived cell used in the present invention is an immortalized cell or a cell line derived from a human tissue. The immortalized cell and the cell line can be prepared by use of methods known to those skilled in the art.

In one embodiment, the human-derived cell used in the present invention is a human-derived induced pluripotent stem cell (iPS cell) or an embryonic stem cell (ES cell). The iPS cell and the ES cell can be prepared by use of methods known to those skilled in the art. In one embodiment, the human-derived cell used in the present invention is a cell derived from a human-derived induced pluripotent stem cell (iPS cell) or an embryonic stem cell (ES cell).

The CD1d used in the present invention can be naturally occurring CD1d or a modified form having its functions. CD1d may be CD1d which is endogenously expressed in the human-derived cell used, or may be CD1d which is exogenously expressed in the human-derived cell used. In one embodiment, the expression means expression at any location of a cell. In one embodiment, the expression means expression on the cell surface. In one embodiment, aAVC expresses exogenous CD1d. In one embodiment, the CD1d used in the present invention is CD1d derived from a mammal (e.g., humans, monkeys, mice, rats, dogs, and chimpanzees). In one embodiment, the CD1d used in the present invention is human CD1d.

In the present specification, the terms "exogenous" or "exogenously" are used interchangeably so as to refer to artificial transfer of a gene or a nucleic acid into a cell of interest by an operation such as genetic engineering or gene transfer, and the gene or the nucleic acid artificially introduced into the cell of interest, or a protein expressed therefrom. The exogenous gene may be operably linked to a promoter sequence which drives the expression of the gene.

In the present specification, the term "endogenous" or "endogenously" means that a cell originally possesses a material, for example, gene, a nucleic acid or a protein.

In the present specification, the term "derived" is used to indicate an animal species from which a cell has been obtained. For example, the human-derived cell means that the cell is a cell obtained from a human or a cell line obtained by subculturing the cell. For example, the human-derived cell means that the cell is a human cell.

In the present specification, the term "identity" means a value of Identity obtained from the parameters provided as defaults using EMBOSS Needle (Nucleic Acids Res.; 2015; 43: W580-W584). The parameters described above are as follows:

Gap Open Penalty=10
Gap Extend Penalty=0.5
Matrix=EBLOSUM62
End Gap Penalty=false In one embodiment, the human CD1d is a protein consisting of the amino acid sequence represented by SEQ ID NO: 4. In one embodiment, the human CD1d is a protein that consists of an amino acid sequence derived from the amino acid sequence represented by SEQ ID NO: 4 with the deletion, substitution, insertion, and/or addition of 1 or several amino acids or in a certain embodiment, 1 to 10, 1 to 7, 1 to 5, 1 to 3, or 1 or 2 amino acids, and has a function of CD1d. In one embodiment, the human CD1d is a protein that consists of an amino acid sequence having at least 90% or more, 95% or more, 96% or more, 97% or more, 98% or more, or 99% or more identity to the amino acid sequence represented by SEQ ID NO: 4, and has a function of CD1d. In one embodiment, the human CD1d is a protein consisting of an amino acid sequence encoded by the nucleotide sequence represented by SEQ ID NO: 3.

Examples of the function of CD1d include the ability to bind to a CD1d ligand (e.g., α-GalCer). The ability of CD1d to bind to a CD1d ligand may be easily evaluated by those skilled in the art using a method known in the art. Alternatively, the function of CD1d may be evaluated by using the ability of aAVC to activate human NKT cells as an index. This ability to activate human NKT cells can be evaluated by a method described in Patent Literature 1 or Example 4 of the present application.

In one embodiment, the aAVC used in the present invention expresses a cancer antigen. An arbitrary protein whose expression is found in cancer cells can be used as the cancer antigen used in the present invention. Examples of cancer antigens include Wilms tumor 1 (WT-1), human carbohydrate antigen 125 (CA-125), carcinoembryonic antigen (CEA), human telomerase reverse transcriptase (hTERT), mucin-1 (Muc-1), mucin-2 (Muc-2), cancer/testis antigen 1B (CTAG1B/NY-ESO-1), prostatic acid phosphatase (PAP), prostate specific antigen (PSA), prostate specific membrane antigen (PSMA), survivin b, mutant ras, and mutant p53. In one embodiment, the cancer antigen used in the present invention is Wilms tumor 1 (WT-1). In one embodiment, the WT-1 is human WT-1. In one embodiment, the human WT-1 is a protein consisting of the amino acid sequence represented by SEQ ID NO: 2. In one embodiment, the human WT-1 is a protein consisting of an amino acid sequence derived from the amino acid sequence represented by SEQ ID NO: 2 with the deletion, substitution, insertion, and/or addition of 1 or several amino acids or in a certain embodiment, 1 to 10, 1 to 7, 1 to 5, 1 to 3, or 1 or 2 amino acids. In one embodiment, the human WT-1 is a protein consisting of an amino acid sequence having at least 90% or more, 95% or more, 96% or more, 97% or more, 98% or more, or 99% or more identity to the amino acid sequence represented by SEQ ID NO: 2. In one embodiment, aAVC expresses one cancer antigen. In one embodiment, aAVC expresses a plurality of cancer antigens. The cancer antigen may be a naturally occurring cancer antigen or a modified form thereof as long as aAVC expressing the cancer antigen exhibits an antitumor effect through an immunological effect against the cancer antigen. The cancer antigen may be an antigen endogenously expressed in the human-derived cell used or may be an antigen exogenously expressed in the human-derived cell used. In one embodiment, aAVC expresses an exogenous cancer antigen. In one embodiment, aAVC expresses a plurality of exogenous cancer antigens.

α-GalCer is one of the CD1d ligands and a substance represented by CAS RN: 158021-47-7 and a molecular formula: $C_{50}H_{99}NO_9$ (molecular weight: 858.34). α-GalCer may be synthesized according to a technique known in the art, or a commercially available product (e.g., α-Galactosylceramide (Funakoshi Co., Ltd., Cat. KRN7000)) may be used. The loading of α-GalCer onto cells may be performed by culturing cells expressing CD1d in a medium containing α-GalCer as described in the section "2. Method for preparing aAVC".

2. Method for Preparing aAVC

The present invention may comprise preparing cells at a stage before loading of α-GalCer (also referred to as aAVC precursor cells in the present specification), and loading α-GalCer onto the aAVC precursor cells. The present invention also provides a method for preparing a cell, wherein the cell expresses exogenous CD1d, and has α-GalCer loaded on the cell surface; wherein the cell is administered to the human such that a single dose of α-GalCer loaded on the cell surface ranges from 1.7 ng to 275 ng per kg body weight of the human; and wherein the method comprises the step of culturing human-derived cells expressing exogenous CD1d in a culture medium containing 56 ng/mL to 3000 ng/mL α-GalCer. The present invention also provides a method for preparing a cell, wherein the cell expresses exogenous CD1d, and has α-GalCer loaded on the cell surface; wherein the cell is administered to the human such that a single dose of α-GalCer loaded on the cell surface ranges from 1.7 ng to 275 ng per kg body weight of the human; and wherein the method comprises the step of culturing human-derived cells expressing exogenous CD1d in a culture medium containing 56 ng/mL to 3000 ng/mL α-GalCer and the step of selecting a cell wherein the amount of α-GalCer loaded on the cell surface is in the range of 3.9 to 275 ng per $1 \times 10^6$ cells.

2-1. Preparation of aAVC Precursor Cell

The aAVC precursor cells can be prepared by introducing either CD1d gene or a gene encoding a cancer antigen, or CD1d gene and a gene encoding a cancer antigen to human-derived cells. The CD1d gene and the gene encoding a cancer antigen can be designed and prepared by use of a standard molecular biological and/or chemical method by obtaining nucleotide sequences encoding amino acid sequences from NCBI RefSeq ID or GenBank Accession numbers. These genes can be synthesized, for example, by use of a phosphoramidite method based on their nucleotide sequences, or can be prepared by combining DNA fragments obtained through polymerase chain reaction (PCR) from cDNA libraries. The transfer of the genes of interest to human-derived cells can be performed using an expression vector containing the gene to be introduced in a form of cDNA, mRNA or the like. Alternatively, the genes of interest may be introduced directly to human-derived cells by a method such as electroporation, lipofection or the like.

Further, after introducing the gene of interest into human-derived cells to prepare aAVC progenitor cells, the cells may be cultured and proliferated.

The expression vector used in the present invention is not particularly limited as long as the expression vector enable to express CD1d or the cancer antigen of interest, or CD1d and the cancer antigen of interest in human-derived cells. The expression vector may be, for example, a plasmid vector (e.g., pcDNA series (Thermo Fisher Scientific Inc.), pAL-TER®-MAX (Promega Corp.), and pHEK293 Ultra Expression Vector (Takara Bio Inc.)), or a viral vector (e.g., lentivirus, adenovirus, retrovirus, and adeno-associated virus). For example, pLVSIN-CMV/EF1α vector (Takara Bio Inc.) or pLenti vector (Thermo Fisher Scientific Inc.) for use in the preparation of lentivirus can be used in the production of a viral vector. When CD1d and a cancer antigen are exogenously expressed in human-derived cells, CD1d and the cancer antigen may be expressed by using either one vector or separate vectors.

The expression vector may contain a promoter operably linked to the gene encoding CD1d or a cancer antigen. As a promoter, any of a promoter which constitutively promotes expression and a promoter that is driven by a drug (e.g., tetracycline or doxycycline) or the like can be used Examples of the promoter constitutively promoting expression include promoters derived from viruses such as CMV (cytomegalovirus), RSV (respiratory syncytial virus), and SV40 (simian virus 40), actin promoter, and EF (elongation factor) 1α promoter. Examples of the inducible promoter include tetracycline responsive factor (TRE3G promoter), cumate operator sequence, λ operator sequence (12×λOp), and heat shock promoter.

The expression vector may contain a start codon and a stop codon. In this case, the expression vector may contain an enhancer sequence, an untranslated region, a splice junction, a polyadenylation site, or a replicable unit, etc. The expression vector may also contain a gene capable of serving as a marker for confirming the expression of the gene of interest (e.g., a drug resistance gene, a gene encoding a reporter enzyme, or a gene encoding a fluorescent protein).

In one embodiment, the aAVC precursor cells are prepared by introducing CD1d gene to human-derived cells using a viral vector. In one embodiment, the aAVC precursor cells used in the present invention is a cell caused to exogenously express CD1d with a viral vector. In this embodiment, the aAVC precursor cells may contain a gene encoding CD1d, the gene being operably linked to a promoter. In one embodiment, the aAVC precursor cells are prepared by introducing CD1d gene and a gene encoding a cancer antigen to human-derived cells using a viral vector. In one embodiment, the aAVC precursor cells used in the present invention is a cell in which CD1d and a cancer antigen have been exogenously expressed using a viral vector. In this embodiment, the aAVC precursor cells may contain CD1d gene and a gene encoding a cancer antigen, the genes being each operably linked to a promoter.

In one embodiment, the aAVC precursor cells are prepared by introducing CD1d gene to human-derived cells using a lentivirus vector. In one embodiment, the aAVC precursor cells used in the present invention is a cell in which CD1d has been exogenously expressed using a lentivirus vector. In one embodiment, the aAVC precursor cells are prepared by introducing CD1d gene and a gene encoding a cancer antigen to human-derived cells using a lentivirus vector. In one embodiment, the aAVC precursor cells used in the present invention is a cell in which CD1d and a cancer antigen have been exogenously expressed using a lentivirus vector.

The aAVC precursor cells are cultured by a method known in the art. For example, MEM medium (Science; 1952; 122: 501), DMEM medium (Virology; 1959; 8: 396-397), RPMI1640 medium (J. Am. Med. Assoc.; 1967; 199: 519-524), 199 medium (Proc. Soc. Exp. Biol. Med.; 1950; 73: 1-8), FreeStyle™ 293 Expression Medium (Thermo Fisher Scientific Inc., Cat. 12338022), CD 293 Medium (Thermo Fisher Scientific Inc., Cat. 11913019), or Expi293™ Expression Medium (Thermo Fisher Scientific Inc., Cat. A1435101) can be used as a basal medium. The culture medium can contain, for example, serum (e.g., fetal bovine serum), a serum replacement (e.g., KnockOut Serum Replacement: KSR), a fatty acid or a lipid, an amino acid, vitamin, a growth factor, a cytokine, an antioxidant, 2-mercaptoethanol, pyruvic acid, a buffer, an inorganic salt, or an antibiotic. The culture conditions (e.g., culture conditions such as culture time, temperature, medium pH, and $CO_2$ concentration) can be appropriately selected by those skilled in the art. The medium pH is preferably approximately 6 to 8. The culture temperature is not particularly limited and is, for example, approximately 30 to 40° C., preferably approximately 37° C. The $CO_2$ concentration is approximately 1 to 10%, preferably approximately 5%. The culture time is not particularly limited, and the culture is performed for approximately 15 to 336 hours. If necessary, aeration or stirring may be performed. In the case of using a promoter that is driven by a drug such as tetracycline or doxycycline, the method may comprise the step of culturing the aAVC precursor cells in a medium supplemented with the drug to induce the expression of CD1d and the cancer antigen. This step can be performed in accordance with a gene induction method using a general gene induction system.

2-2. Loading of α-GalCer onto Cell aAVC having α-GalCer loaded on the cell surface is prepared by pulsing the aAVC precursor cells with α-GalCer. In the present specification, the phrase "having α-GalCer loaded on the cell surface" refers to a state where α-GalCer is bound to the surface of an aAVC cell. The amount of α-GalCer bound can be measured by use of a method described in the section "2-3. Measurement of amount of α-GalCer loaded on aAVC". In the present specification, the term "pulsing" with α-GalCer refers to contacting aAVC precursor cells with α-GalCer to bind the α-GalCer to the cell surface of the aAVC precursor cells expressing CD1d. The pulsing can be performed in a cell culture medium.

The conditions for pulsing the aAVC precursor cells (e.g., the timing of adding α-GalCer to a cell culture medium, the concentration of α-GalCer in the culture medium and culture time) can be appropriately adjusted by those skilled in the art in consideration of the aAVC precursor cells used and culture conditions. The concentration of α-GalCer to be added to the culture medium for the aAVC precursor cells is not particularly limited and can be appropriately selected within the range of, for example, 56 ng/mL to 3000 ng/mL.

The preparation of the aAVC precursor cells and the pulsing of the cells with α-GalCer may be performed at the same time by the gene introduction of CD1d or a cancer antigen or CD1d and a cancer antigen to human-derived cells in the presence of α-GalCer.

After the loading of α-GalCer onto the cell surface, α-GalCer that has not been loaded onto the cell surface (an excess of α-GalCer in the culture medium) can be removed.

After pulsing the aAVC precursor cells with α-GalCer, the proliferation of aAVC may be arrested by using an artificial method. The method for arresting the proliferation of aAVC is not particularly limited. For example, a method of arresting cell proliferation by exposure to radiation of particle lays such as radioactive rays (e.g., X-ray or γ-ray), or a method of adding a drug such as mitomycin C may be used.

2-3. Measurement of the Amount of α-GalCer Loaded on aAVC

The present inventors have established a method for measuring the amount of α-GalCer loaded on aAVC cell surface. The measurement of the amount of α-GalCer loaded on aAVC cell surface can be performed by preparing cell extracts of aAVC and quantifying α-GalCer in the extracts by a method using mass spectrometry (MS) (e.g., liquid chromatography-tandem mass spectrometry (LC-MS/MS)).

In a general quantitative analysis using LC-MS/MS, the quantitative analysis of α-GalCer in a sample is conducted by the following steps.

Step 1: Standard substances of α-GalCer prepared at several concentrations are analyzed.
Step 2: Temporal change in ionic strength (mass chromatogram) is obtained for m/z (mass/charge ratio) of ions derived from the standard substances, and peak areas of the mass chromatogram are calculated. Step 3: A calibration curve is prepared from the relationship between the peak area of each substance determined in the step 2 and the concentration of the substance.
Step 4: A sample to be quantified is analyzed to calculate the mass chromatogram peak area of α-GalCer in the sample.
Step 5: The concentration of α-GalCer in the sample corresponding to the peak area in the mass chromatogram of the step 4 is calculated on the basis of the calibration curve prepared in the step 3.

The measurement of α-GalCer by LC-MS/MS can be performed by, for example, a method of ionizing α-GalCer into precursor ions and product ions by an electrospray ionization method. The column and the composition of the mobile phase for use in liquid chromatography in LC-MS/MS may be any combination of a column and a mobile phase as long as the combination used permits separation of α-GalCer from cell-derived components and permits discrimination of α-GalCer from cell-derived components by MS/MS.

In one embodiment, the amount of α-GalCer loaded on the aAVC cell surface is in the range of 3.9 ng to 275 ng per $1 \times 10^6$ cells. In one embodiment, the amount of α-GalCer loaded on the aAVC cell surface can be in the range of 10 to 275 ng, 10 to 140 ng or 10 to 100 ng per $1 \times 10^6$ cells.

3. Treatment or Prevention of Cancer with aAVC

The treatment or prevention method of the present invention can involve administration to a subject such that the single dose of α-GalCer loaded on the cell surface of aAVC to be administered to a human is a predetermined dose.

In one embodiment, the treatment or prevention method of the present invention is characterized in that an aAVC is administered to a subject such that the single dose of α-GalCer loaded on the cell surface of aAVC to be administered to a human ranges from 1.7 ng to 275 ng per kg body weight of the human.

In one embodiment, the single dose of α-GalCer loaded on the cell surface of aAVC to be administered to a human can be in a particular numeric range. The particular numeric range can be a numeric range included in the range of 1.7 ng to 275 ng (i.e., a numeric range from an upper limit value of 275 ng or less to a lower limit value of 1.7 ng or more) per kg body weight of the human. The numeric range has, for example, a numeric value of 275 ng or less, 270 ng or less, 260 ng or less, 250 ng or less, 240 ng or less, 238 ng or less, 230 ng or less, 220 ng or less, 210 ng or less, 200 ng or less, 190 ng or less, 180 ng or less, 170 ng or less, 160 ng or less, 150 ng or less, 140 ng or less, 130 ng or less, 120 ng or less, 110 ng or less, 100 ng or less, 90 ng or less, 80 ng or less, 70 ng or less, 66 ng or less, 60 ng or less, 50 ng or less, 47 ng or less, 40 ng or less, 36 ng or less, 30 ng or less, 24 ng or less, 20 ng or less, 19 ng or less, 18 ng or less, 17 ng or less, 16 ng or less, 15 ng or less, 14 ng or less, 13 ng or less, 12 ng or less, 11 ng or less, 10 ng or less, 9 ng or less, 8 ng or less, 7 ng or less, 6.6 ng or less, 5 ng or less, 4.7 ng or less, 4 ng or less, 3.6 ng or less, 3 ng or less, or 2 ng or less as its upper limit value and a numeric value of 270 ng or more, 260 ng or more, 250 ng or more, 240 ng or more, 238 ng or more, 230 ng or more, 220 ng or more, 210 ng or more, 200 ng or more, 190 ng or more, 180 ng or more, 170 ng or more, 160 ng or more, 150 ng or more, 140 ng or more, 130 ng or more, 120 ng or more, 110 ng or more, 100 ng or more, 90 ng or more, 80 ng or more, 70 ng or more, 66 ng or more, 60 ng or more, 50 ng or more, 47 ng or more, 40 ng or more, 36 ng or more, 30 ng or more, 24 ng or more, 20 ng or more, 19 ng or more, 18 ng or more, 17 ng or more, 16 ng or more, 15 ng or more, 14 ng or more, 13 ng or more, 12 ng or more, 11 ng or more, 10 ng or more, 9 ng or more, 8 ng or more, 7 ng or more, 6.6 ng or more, 6 ng or more, 5 ng or more, 4.7 ng or more, 4 ng or more, 3.6 ng or more, 3 ng or more, 2.4 ng or more, 2 ng or more, or 1.7 ng or more as a lower limit value. The particular numeric range can be a numeric range included in one or more ranges selected from the group consisting of, for example, the range of 1.7 ng to 50 ng, the range of 50 ng to 100 ng, the range of 100 ng to 150 ng, the range of 150 ng to 200 ng, the range of 200 ng to 275 ng, the range of 1.7 ng to 238 ng, the range of 1.7 ng to 170 ng, the range of 6.6 ng to 238 ng, or the range of 6.6 ng to 170 ng.

In one embodiment, the amount of α-GalCer loaded on the cell surface of aAVC to be administered to a human may be determined by using the proportion of NKT cells in spleen cells in the subject after administration as an index. An elevated proportion of NKT cells in spleen cells is considered to enhance the effect of administration.

In one embodiment, the amount of α-GalCer loaded on the cell surface of aAVC to be administered to a human is in the range of 3.9 ng to 275 ng per $1 \times 10^6$ cells. In one embodiment, the amount of α-GalCer loaded on the cell surface of aAVC to be administered to a human can be in the range of 10 to 275 ng, 10 to 140 ng or 10 to 100 ng per $1 \times 10^6$ cells.

aAVC can be administered to a subject in need of treatment or prevention of a cancer by use of a method known to those skilled in the art. In the case of administering aAVC to a subject, the aAVC can be administered to the subject in the form of a pharmaceutical composition comprising aAVC and a pharmaceutically acceptable excipient. The pharmaceutical composition comprising aAVC can be prepared by a commonly used method using an excipient commonly used in the art, i.e., an pharmaceutical excipient, a pharmaceutical carrier, or the like. For the formulation of the pharmaceutical composition, an excipient, a carrier, an additive, or the like appropriate for its dosage form can be used within a pharmaceutically acceptable range. Examples of the dosage form of the pharmaceutical composition include parenteral agents such as injections and infusions.

Examples of the cancer to be targeted by the treatment or prevention of the present invention include, but are not particularly limited to: hematologic cancers such as acute lymphoblastic leukemia (ALL), acute myeloid leukemia (AML), Hodgkin's lymphoma, non-Hodgkin's lymphoma, B cell lymphoma, multiple myeloma, and T cell lymphoma; solid cancers such as myelodysplastic syndrome, adenocarcinoma, squamous cell carcinoma, adenosquamous carcinoma, anaplastic cancer, large-cell cancer, non-small cell lung cancer, small-cell lung cancer, mesothelioma, skin cancer, breast cancer, prostate cancer, bladder cancer, vaginal cancer, neck cancer, head and neck cancer, uterine cancer, uterine cervical cancer, liver cancer, gallbladder cancer, bile duct cancer, kidney cancer, pancreatic cancer, lung cancer, colon cancer, colorectal cancer, rectum cancer, small intestinal cancer, stomach cancer, esophageal cancer, testis cancer, ovary cancer, bladder cancer, and brain tumor; cancers of bone tissues, cartilage tissues, adipose tissues, muscle tissues, vascular tissues and hematopoietic tissues; sarcomas such as chondrosarcoma, Ewing's sarcoma, malignant hemangioendothelioma, malignant schwannoma, osteosarcoma, and soft tissue sarcoma; and blastomas such as hepatoblastoma, medulloblastoma, nephroblastoma, neuroblastoma, pancreatoblastoma, pleuropulmonary blastoma, and retinoblastoma.

The dose of aAVC to a human and the number of doses thereof can be appropriately adjusted according to the type, position, and severity of the cancer, the age, body weight and condition of the subject to be treated, etc. The dose of aAVC can be set to an arbitrary amount within the range of, for example, $1 \times 10^3$ cells/kg to $1 \times 10^8$ cells/kg per dose to a subject. In one embodiment, the dose of aAVC is $1.7 \times 10^3$ cells/kg, $1.7 \times 10^4$ cells/kg, $1.7 \times 10^5$ cells/kg, or $1.7 \times 10^6$ cells/kg. In one embodiment, the dose of aAVC can be set to an arbitrary amount within the range of $6.2 \times 10^3$ cells/kg to $7.0 \times 10^7$ cells/kg. In this context, the lower limit value is the number of cells per kg body weight of the human when cells having α-GalCer loaded in an amount of $275$ ng/$10^6$ cells are administered such that the single dose of α-GalCer loaded on the cell surface is $1.7$ ng/kg. The upper limit value is the number of cells per kg body weight of the human when cells having α-GalCer loaded in an amount of $3.9$ ng/$10^6$ cells are administered such that the single dose of α-GalCer loaded on the cell surface is $275$ ng/kg. In one embodiment, the dose of aAVC can be in a particular numeric range. The particular numeric range can be a numeric range included in the range of $6.2 \times 10^3$ cells/kg to $7.0 \times 10^7$ cells/kg (i.e., a numeric range from an upper limit value of $7.0 \times 10^7$ cells/kg or less to a lower limit value of $6.2 \times 10^3$ cells/kg or more). The numeric range has, for example, a numeric value of $7.0 \times 10^7$ cells/kg or less, $6.0 \times 10^7$ cells/kg or less, $5.0 \times 10^7$ cells/kg or less, $4.0 \times 10^7$ cells/kg or less, $3.0 \times 10^7$ cells/kg or less, $2.0 \times 10^7$ cells/kg or less, $1.7 \times 10^7$ cells/kg or less, $1.3 \times 10^7$ cells/kg or less, $1.0 \times 10^7$ cells/kg or less, $9.0 \times 10^6$ cells/kg or less, $8.0 \times 10^6$ cells/kg or less, $7.0 \times 10^6$ cells/kg or less, $6.0 \times 10^6$ cells/kg or less, $5.0 \times 10^6$ cells/kg or less, $4.3 \times 10^6$ cells/kg or less, $4.0 \times 10^6$ cells/kg or less, $3.0 \times 10^6$ cells/kg or less, $2.7 \times 10^6$ cells/kg or less, $2.0 \times 10^6$ cells/kg or less, $1.7 \times 10^6$ cells/kg or less, or $1.0 \times 10^6$ cells/kg or less as its upper limit value and a numeric value of $1.0 \times 10^4$ cells/kg or more, $1.7 \times 10^4$ cells/kg or more, $2.0 \times 10^4$ cells/kg or more, $3.0 \times 10^4$ cells/kg or more, $4.0 \times 10^4$ cells/kg or more, $4.4 \times 10^4$ cells/kg or more, $5.0 \times 10^4$ cells/kg or more, $6.0 \times 10^4$ cells/kg or more, $6.6 \times 10^4$ cells/kg or more, $7.0 \times 10^4$ cells/kg or more, $8.1 \times 10^4$ cells/kg or more, $9.0 \times 10^4$ cells/kg or more, $1.0 \times 10^5$ cells/kg or more, $1.7 \times 10^5$ cells/kg or more, $2.0 \times 10^5$ cells/kg or more, $3.0 \times 10^5$ cells/kg or more, $3.2 \times 10^5$ cells/kg or more, $4.0 \times 10^5$ cells/kg or more, $5.0 \times 10^5$ cells/kg or more, $6.0 \times 10^5$ cells/kg or more, $6.6 \times 10^5$ cells/kg or more, $7.0 \times 10^5$ cells/kg or more, $8.0 \times 10^5$ cells/kg or more, or $9.0 \times 10^5$ cells/kg or more as a lower limit value. The particular numeric range can be a numeric range included in one or more ranges selected from the group consisting of, for example, the ranges of $1.7 \times 10^3$ cells/kg to $1.7 \times 10^6$ cells/kg, $1.7 \times 10^3$ cells/kg to $1.7 \times 10^5$ cells/kg, $1.7 \times 10^3$ cells/kg to $1.7 \times 10^4$ cells/kg, $1.7 \times 10^4$ cells/kg to $1.7 \times 10^6$ cells/kg, $1.7 \times 10^4$ cells/kg to $1.7 \times 10^5$ cells/kg, $1.7 \times 10^5$ cells/kg to $1.7 \times 10^6$ cells/kg, $6.6 \times 10^4$ cells/kg to $1.7 \times 10^7$ cells/kg, $1.7 \times 10^5$ cells/kg to $2.7 \times 10^7$ cells/kg, $6.6 \times 10^5$ cells/kg to $1.7 \times 10^7$ cells/kg, $8.1 \times 10^4$ cells/kg to $1.3 \times 10^7$ cells/kg, $3.2 \times 10^5$ cells/kg to $8.0 \times 10^6$ cells/kg, $4.4 \times 10^4$ cells/kg to $7.0 \times 10^6$ cells/kg, $4.4 \times 10^4$ cells/kg to $7.0 \times 10^6$ cells/kg, $2.6 \times 10^5$ cells/kg to $4.3 \times 10^6$ cells/kg, $1.7 \times 10^4$ cells/kg to $2.7 \times 10^6$ cells/kg, and $6.6 \times 10^4$ cells/kg to $1.7 \times 10^6$ cells/kg.

As for a method for administering aAVC to a human, the aAVC can be administered by, for example, intravenous, intratumoral, intradermal, subcutaneous, intramuscular, intraperitoneal, or intra-arterial injection or infusion.

The treatment or prevention method of the present invention can be used in combination with an additional cancer treatment method. Examples of the additional cancer treatment method include surgery, radiotherapy, hematopoietic stem cell transplantation, and treatment with other anticancer agents.

<Pharmaceutical Composition, etc. of Present Invention>

The present invention also provides a pharmaceutical composition for the treating or preventing a cancer, comprising a human-derived cell. The pharmaceutical composition comprises a human-derived cell that expresses exogenous or endogenous CD1d and has α-GalCer loaded on the cell surface, and is administered to a human such that a single dose of α-GalCer loaded on the surface of the cell to be administered to the human ranges from $1.7$ ng to $275$ ng per kg body weight of the human. The human-derived cell may further express one or more exogenous or endogenous cancer antigen(s). The present invention also provides use of a human-derived cell for manufacturing a pharmaceutical composition for the treatment or prevention of a cancer, wherein the cell expresses exogenous or endogenous CD1d and has α-GalCer loaded on the cell surface, and the composition is administered to a human such that a single dose of α-GalCer loaded on the surface of the cell to be administered to the human ranges from $1.7$ ng to $275$ ng per kg body weight of the human. The human-derived cell may further express one or more exogenous or endogenous cancer antigen(s). The present invention also provides a human-derived cell for the treatment or prevention of a cancer, wherein the cell expresses exogenous or endogenous CD1d and has α-GalCer loaded on the cell surface, and the cell is administered to a human such that a single dose of α-GalCer loaded on the surface of the cell to be administered to the human ranges from $1.7$ ng to $275$ ng per kg body weight of the human. The human-derived cell may further express one or more exogenous or endogenous cancer antigen(s).

Embodiments regarding the cell used (aAVC) and a method for producing the same, and its use in the treatment or prevention of a cancer, etc. in the pharmaceutical composition, the use, and the cell of the present invention mentioned above are as described in the section "Method for treating or preventing cancer according to the present invention".

<Method for Producing Pharmaceutical Composition, etc. According to the Present Invention>

The present invention also provides a method for producing a pharmaceutical composition for treating or preventing a cancer, comprising a human-derived cell. The method for producing a pharmaceutical composition according to the present invention can be a method comprising: providing a human-derived cell that expresses exogenous or endogenous CD1d and has α-GalCer loaded on the cell surface; and packaging the cell as a pharmaceutical composition that is administered to a human such that a single dose of α-GalCer loaded on the cell surface is in the range of 1.7 ng to 275 ng per kg body weight of the human. The method may further comprise the step of arresting the growth of the human-derived cell by a method such as exposure to radiation. In one embodiment, the method for producing a pharmaceutical composition according to the present invention can be a method comprising: providing a human-derived cell that expresses exogenous or endogenous CD1d and has α-GalCer loaded on the cell surface; selecting a cell or determining a cell number to be packaged as a pharmaceutical composition by using the amount of α-GalCer loaded on the cell surface as an index; and packaging the selected or determined cell to obtain a pharmaceutical composition. In this embodiment, the total amount of α-GalCer loaded on the surface of cells contained in the pharmaceutical composition can be in a numeric range defined by multiplying an arbitrary numeric value from 1.7 ng to 275 ng by an average human body weight. The method for producing a pharmaceutical composition according to the present invention may further involve a method for measuring the amount of α-GalCer loaded on cell surface, described in the section <Method for measuring amount of α-GalCer loaded on cell>. The method for producing a pharmaceutical composition according to the present invention may further comprise: selecting a cell population wherein the amount of α-GalCer loaded per cell is in a defined numeric range; and packaging the selected cell population as a pharmaceutical composition. The amount of α-GalCer loaded per cell can be in the range of, for example, 3.9 ng to 275 ng, 10 to 275 ng, 10 to 140 ng or 10 to 100 ng per $1 \times 10^6$ cells. The produced pharmaceutical composition is administered at the dose described above to a human.

<Method for Measuring Amount of α-GalCer Loaded on Cell>

The present invention also provides the following method for measuring the amount of α-GalCer loaded on cells:

a method for measuring the amount of α-GalCer loaded on cells, wherein the cells express CD1d and have α-GalCer loaded on the cell surface, wherein the method comprises the steps of:

preparing cell extracts of the cells; and subjecting the cell extracts to mass spectrometry (MS) to measure the amount of α-GalCer in the extracts.

In one embodiment, the mass spectrometry (MS) is liquid chromatography-tandem mass spectrometry (LC-MS/MS).

In one embodiment, the cells used in this method are human-derived cells that express exogenous or endogenous CD1d and have α-GalCer loaded on the cell surface (aAVC). In one embodiment, the cells used in this method are human-derived cells that express exogenous or endogenous CD1d and one or more exogenous or endogenous cancer antigen(s) and have α-GalCer loaded on the cell surface (aAVC). In one embodiment, the cells used in this method are human-derived cells that express exogenous CD1d and one or more exogenous cancer antigen(s) and have α-GalCer loaded on the cell surface (aAVC).

Particular Examples to be referred to will be provided here for the further understanding of the present invention. However, these examples are given for illustrative purposes and do not limit the present invention.

EXAMPLES

Example 1-1: Preparation of aAVC-WT1

Lentiviruses were prepared using plasmids carrying WT1, CD1d, and Tet3G (reverse tetracycline regulatory transactivator) genes, respectively. By introducing those genes into FreeStyle™ 293-F cells (Thermo Fisher Scientific, Cat. R79007) using said lentivirus carrying each of the genes, aAVC expressing CD1d and WT1 and loaded α-GalCer onto the cell surface was constructed.

(1) Construction of Plasmids for Lentivirus Preparation

A gene having a 5'-terminally added XhoI recognition sequence and a 3'-terminally added NotI recognition sequence in the WT1 gene (SEQ ID NO: 1) was inserted into the XhoI-NotI site of pLVSIN-CMV Pur plasmid (Takara Bio Inc., Cat. 6183) to construct pLVSIN-CMV-WT1 plasmid. The gene of SEQ ID NO: 1 was prepared by optimization for human codons through the artificial gene synthesis service of Thermo Fisher Scientific Inc. based on the amino acid sequence of Wilms tumor protein isoform D (NCBI Reference Sequence: NP_077744.3). The pLVSIN-CMV-WT1 plasmid was cleaved with restriction enzymes ClaI and EcoRI to remove CMV promoter. Then, the cut ends were blunted with T4 DNA Polymerase (Toyobo Co., Ltd., Cat. TPL-101). Ligation reaction was performed using DNA Ligation Kit (Takara Bio Inc., Cat. 6023) to construct pLVSIN-Δ-WT1 plasmid. TRE3G promoter excised from pTRE3G (Takara Bio Inc., Cat. 631173) with restriction enzymes EcoRI and SalI was inserted to the EcoRI-XhoI site of the pLVSIN-Δ-WT1 plasmid to construct pLVSIN-TRE3G-WT1 plasmid. The pLVSIN-TRE3G-WT1 plasmid was cleaved with restriction enzymes BamHI and MluI to remove PGK promoter and puromycin resistance gene. Then, the cut ends of the plasmid were blunted with T4 DNA Polymerase. Ligation reaction was performed using DNA Ligation Kit to construct pLVSIN-TRE3G-WT1Δpur plasmid.

pLVSIN-CMV Pur plasmid was cleaved with restriction enzymes XhoI and MluI to remove PGK promoter and puromycin resistance gene. The CD1d gene (SEQ ID NO: 3) was amplified by PCR using primers with sequences complementary to 15 nucleotides at both sides of the XhoI-MluI site of the plasmid, respectively. The amplified CD1d gene was inserted into the cleaved plasmid described above using In-Fusion® HD Cloning Kit (Takara Bio Inc., Cat. 639648) to construct pLVSIN-CMV-CD1dΔpur plasmid. The gene of SEQ ID NO: 3 was prepared by optimization for human codons through the artificial gene synthesis service of Thermo Fisher Scientific Inc. based on the amino acid sequence (SEQ ID NO: 4) of antigen-presenting glycoprotein CD1d isoform 1 precursor (NCBI Reference Sequence: NP_001757.1).

The Tet3G gene was amplified from pCMV-Tet-On 3G plasmid (Takara Bio Inc., Cat. 631335) by use of PCR. The amplified gene was inserted to the XhoI-MluI site of pLVSIN-CMV Pur plasmid using In-Fusion® HD Cloning Kit to construct pLVSIN-CMV-Tet3GΔpur plasmid.

(2) Lentivirus Preparation

WT1-loaded lentivirus, CD1d-loaded lentivirus and Tet3G-loaded lentivirus were prepared using the pLVSIN-TRE3G-WT1Δpur plasmid, the pLVSIN-CMV-CD1dΔpur plasmid, and the pLVSIN-CMV-Tet3GΔpur plasmid prepared in (1).

30 μg of the pLVSIN-TRE3G-WT1Δpur plasmid and 30 μL of ViraPower Lentiviral Packaging Mix (Thermo Fisher Scientific Inc., Cat. K497500) were mixed. Opti-MEM™ I Reduced Serum Medium (Thermo Fisher Scientific Inc., Cat. 31985-070) was added thereto for adjustment to 1 mL and mixed, and the mixture was left standing for 5 minutes (A). 60 µL of PEIpro® in vitro DNA transfection reagent (Polyplus-transfection SE, Cat. 115-010) and 940 µL of Opti-MEM™ I Reduced Serum Medium were mixed and left standing for 5 minutes (B). The (A) and (B) were mixed and left standing at room temperature for 15 minutes. Then, gene introduction was performed by adding the whole amount to 293T cells (ATCC Cat. CRL-3216) inoculated to Falcon® Vent Cap Type Flask 800 mL, Slant Neck (Corning Inc., Cat. 353138). The inoculation of the 293T cells was performed on the day before gene introduction. The cells were cultured at 37° C. under 5% $CO_2$ conditions in DMEM medium (Thermo Fisher Scientific Inc., Cat. 10569-010) containing 10% fetal bovine serum (SAFC Biosciences, Cat. 12007C (γ ray-irradiated product)) and 0.1% gentamicin (Thermo Fisher Scientific Inc., Cat. 15750-060). After the gene introduction, the cells were cultured for 2 days. A culture supernatant containing WT1 gene-loaded lentivirus was recovered by centrifuging the culture medium at 230×g at room temperature for 5 minutes. The supernatant was filtered through a 0.22 µm filter (Merck KGaA, Cat. SLGV033RS). A 4×PEG solution (32% Poly(ethylene glycol) BioUltra, 6000 (Merck KGaA, Cat. 81253-250G), 0.4 M NaCl (Kanto Chemical Co., Inc., Cat. 37144-02), and 0.04 M HEPES (Thermo Fisher Scientific Inc., Cat. 15630-080)) was added thereto in an amount of ⅓ of the amount of the supernatant, mixed, and left standing overnight at 4° C. The mixture was centrifuged at 2500×g at 4° C. for 30 minutes and the supernatant was removed. The supernatant was completely removed after an additional centrifugation at 2500×g at 4° C. for 30 minutes. The precipitates were suspended in an appropriate amount of Opti-MEM™ I Reduced Serum Medium. A recovered culture supernatant was concentrated 30-fold to obtain WT1-loaded lentivirus.

The Tet3G-loaded lentivirus was prepared with almost the same procedure as above using the pLVSIN-CMV-Tet3GΔpur plasmid. The culture period after gene introduction was set to 2 days or 3 days. The still standing after mixing with the 4×PEG solution was carried out at 4° C. overnight or for 4 days. FreeStyle 293 Expression Medium (Thermo Fisher Scientific Inc., Cat. 12338018) was used as the final suspension medium.

12 µg of the pLVSIN-CMV-CD1dΔpur plasmid and 36 µL of ViraPower Lentiviral Packaging Mix were mixed. OptiPro™ SFM (Thermo Fisher Scientific Inc., Cat. 12309-019) was added thereto for adjustment to 6 mL and mixed, and the mixture was left standing for 5 minutes (A-2). 144 µL of Lipofectamine 2000 CD Transfection Reagent (Thermo Fischer Scientific Inc., Cat. 12566-014) and 6 mL of OptiPro™ SFM were mixed and left standing for 5 minutes (B-2). The A-2 and B-2 were mixed and left standing at room temperature for 20 minutes. Then, gene introduction was performed by adding the whole amount to 293FT cells (Thermo Fisher Scientific Inc., Cat. R70007) inoculated to Falcon® Vent Cap Type Flask 800 mL, Slant Neck. The medium used for culturing the 293FT cells was prepared by adding G418 (Thermo Fisher Scientific Inc., Cat. 10131-027) and MEM Non-Essential Amino Acids Solution (100×) (Thermo Fisher Scientific Inc., Cat. 11140050) at final concentrations of 500 µg/mL and 0.1 mM, respectively, to DMEM medium containing 10% fetal bovine serum (SAFC Biosciences, Cat. 12007C (γ ray-irradiated product)) and 0.1% gentamicin. After the gene introduction, the cells were cultured for 2 days. A culture supernatant containing CD1d gene-loaded lentivirus was recovered by centrifuging the culture medium at 540×g at 4° C. for 10 minutes. The supernatant was filtered through a 0.44 µm filter (Merck KGaA, Cat. SLHV033RS). PEG-it™ Virus Precipitation Solution (5×) (System Biosciences, LLC, Cat. LV825A-1) was added thereto in an amount of ⅕ of the amount of the supernatant, mixed, and left standing overnight at 4° C. The mixture was centrifuged at 1500×g at 4° C. for 30 minutes for removal of a supernatant, and centrifuged again at 1500×g at 4° C. for 5 minutes to completely remove the supernatant. The pellets were suspended in an appropriate amount of FreeStyle 293 Expression Medium. A recovered culture supernatant was concentrated 75-fold to obtain CD1d-loaded lentivirus.

(3) Preparation of FreeStyle 293F_WT1_CD1d_Tet3G Cell

FreeStyle™ 293-F cells were infected sequentially with the 3 types of lentiviruses prepared in (2) to obtain FreeStyle 293F_WT1_CD1d_Tet3G cells. The FreeStyle™ 293-F cells were cultured in FreeStyle 293 Expression Medium containing 0.1% gentamicin. The FreeStyle™ 293-F cells at a concentration of 1×10⁶ cells/mL were prepared and inoculated at a volume of 1 mL/well to Falcon® 12-Well Flat Bottom Multiwell Cell Culture Plate with Lid (Corning Inc., Cat. 353043; hereinafter, referred to as a 12-well plate). 50 µL of the WT1-loaded lentivirus and 100 µL of the Tet3G-loaded lentivirus prepared in (2) were added to each well. After centrifugation at 540×g at room temperature for 30 minutes, the cells were gently suspended by pipetting, and shake-cultured. After 3 days, the cells were passaged from the 12-well plate to Corning® Polycarbonate 125 mL Erlenmeyer Flask with Vent Cap (Corning Inc., Cat. 431143; hereinafter, referred to as a 125 mL Erlenmeyer flask), further passaged at 3-day or 4-day intervals, and cultured for 11 days. These cells were inoculated again to a 12-well plate. 100 µL of the CD1d-loaded lentivirus prepared in (2) was added to each well. The second lentivirus infection was performed by the same procedures as in the first one. After 1 day, the cells were passaged from the 12-well plate to a 125 mL Erlenmeyer flask, further passaged at 3-day or 4-day intervals, and cultured for 10 days. The obtained cells were used as FreeStyle 293F_WT1_CD1d_Tet3G cells.

(4) Cloning

Single-cell cloning was performed by the limiting dilution method from the FreeStyle 293F_WT1_CD1d_Tet3G cells prepared in (3). Clones stably expressing all the genes were selected. The cells were inoculated at 1 cell/well to a 96-well plate and passaged as the cells proliferated. The expression levels of the WT1 protein and the CD1d protein in the proliferated cells were measured by ELISA for WT1 and by flow cytometry for CD1d to select clones stably expressing the WT1 and CD1d proteins. The expression of WT1 was induced via Tet-On System by the addition of doxycycline (Takara Bio Inc., Cat. 631311) with a final concentration of 100 ng/mL to the medium, and evaluated. The measurement by ELISA was performed in accordance with a general procedure of sandwich ELISA using Anti-Wilms' tumor Antibody, NT clone 6F-H2 (Merck KGaA, Cat. MAB4234-C) as an antibody for immobilization, Anti WT1 antibody (Wuxi AppTec Co., Ltd., Cat. AP11964c) as a primary antibody, and Rabbit IgG Horseradish Peroxidase-conjugated Antibody (R&D Systems, Inc., Cat. HAF008) as a secondary antibody. The measurement by flow cytometry was performed using APC Mouse Anti-Human CD1d antibody (BD Biosciences, Cat. 563505) and FACSVerse™ (BD Biosciences). The selected clones were used as aAVC-WT1 precursor cells.

(5) Preparation of aAVC-WT1 Differing in Amount of α-GalCer Loaded

By adding various concentrations of α-GalCer (whose synthesis was commissioned by Juzen Chemical Corp. under manufacturing agreement) to aAVC-WT1 precursor cells and culturing the cells, aAVCs differing in the amount of α-GalCer loaded (also referred to as aAVC-WT1) are prepared.

The aAVC-WT1 precursor cells were cultured, and doxycycline at a final concentration of 100 ng/mL and an α-GalCer solution at a final concentration of 56 ng/mL, 167 ng/mL, 500 ng/mL, 1500 ng/mL or 3000 ng/mL were added to the medium to pulse the cells with α-GalCer. The culture of the aAVC-WT1 precursor cells supplemented with the 1500 ng/mL α-GalCer solution was independently performed with three different culture volumes. The α-GalCer solution was prepared by a method conforming to Example 2(1) described later. 2 days after addition of α-GalCer, the cells were recovered by the centrifugation method, washed, concentrated, and irradiated with X-ray at a dose of 30, 40 or 100 Gy using X-ray irradiation apparatus MBR-1520R-3 or MBR-1520R-4 (Hitachi Power Solutions Co., Ltd.) to prepare aAVC-WT1.

Example 1-2: Preparation of Mouse-Type aAVC(3T3)-WT1

Mouse-type aAVC (also referred to as aAVC(3T3)-WT1) was prepared by introducing mRNAs of the WT1 gene and the CD1d gene into mouse NIH/3T3 cells (ATCC, Cat. CRL-1658), and adding α-GalCer (synthesized by Juzen Chemical Corp. under manufacturing agreement) thereto.

The WT1 gene excised from pcDNA3-ATG-WT1 described in WO2013/018778 with restriction enzymes HindIII and EcoRI was inserted into the HindIII-EcoRI site of pGEM-4Z plasmid (Promega Corp., Cat. P2161) to prepare pGEM-4Z-WT1 plasmid. Mouse CD1d gene consisting of the nucleotide sequence shown in SEQ ID NO: 5 (synthesized by optimization for mouse codons through the artificial gene synthesis service of Thermo Fisher Scientific Inc. based on the amino acid sequence (SEQ ID NO: 6) of Antigen-presenting glycoprotein CD1d1, UniProt: P11609-1 was inserted into the HindIII-BamHI site of the pGEM-4Z plasmid to construct pGEM-4Z-mCD1d plasmid. The pGEM-4Z-WT1 plasmid and the pGEM-4Z-mCD1d plasmid were cleaved and linearized with EcoRI and BamHII, respectively. WT1 mRNA and CD1d mRNA were prepared using the plasmids as templates using mMESSAGE mMACHINE™ T7 ULTRA Transcription Kit (Thermo Fisher Scientific Inc., Cat. AMB13455). NIH/3T3 cells cultured for 2 days in Dulbecco's Modified Eagle medium (Thermo Fisher Scientific Inc., Cat. 10569) containing 10% fetal bovine serum supplemented with 500 ng/mL α-GalCer (synthesized by Juzen Chemical Corp. under manufacturing agreement) were recovered. WT1 mRNA and CD1d mRNA were added to the cell suspension and electroporated (poring pulse: voltage: 150 V, pulse width: 8 ms, pulse interval: 50 ms, the number of times: 2, decay rate: 40%, polarity: +, transfer pulse: voltage: 20 V, pulse width: 50 ms, pulse interval: 50 ms, the number of times: ±5, decay rate: 10%, polarity: +/−) using NEPA21 electroporator (Nepa Gene Co., Ltd.). The electroporated cells were recovered and irradiated with X-ray at a dose of 30 Gy using X-ray irradiation system MBR-1520R-3 (Hitachi Power Solutions Co., Ltd.) or MBR-1520R-4 to prepare aAVC(3T3)-WT1.

Example 2: Measurement of Concentration of α-GalCer Loaded on aAVC-WT1 and aAVC(3T3)-WT1

(1) Preparation of α-GalCer Standard Solution 28 g of sucrose (Merck KGaA, Cat. 57903) and 3.75 g of L-histidine (Merck KGaA, Cat. H8000) were added to 400 mL of water for injection (Thermo Fisher Scientific Inc., Cat. A12873-02) and dissolved by heating in a constant temperature water bath at 80° C. 100 mg of α-GalCer and 25 g of 10% polysorbate 20 (MP Biomedicals, LLC, Cat. 194724) were added to the solution, and the mixture was heated for over 1 hour in a constant temperature bath at 80° C. After confirmation that solid matter in the solution was dissolved, the amount was adjusted to 500 g by the addition of water for injection. This solution was used as a 200 μg/mL α-GalCer solution. The 200 μg/mL α-GalCer solution was diluted with a diluent solution (10% water and 90% mobile phase B (70% ethanol, 29.5% methanol, and 0.5% formic acid)) to prepare α-GalCer solutions having a concentration of 1000 ng/mL, 500 ng/mL, 100 ng/mL, 50 ng/mL, 10 ng/mL, 5 ng/mL, or 2.5 ng/mL, which were used as α-GalCer standard solutions.

(2) Preparation of Cell Extract 1 mL or 0.25 mL of Milli-Q water was added to 1×10$^6$ cells of aAVCs prepared by pulsing with various concentration of α-GalCer in Example 1. The cells were homogenized for 20 seconds by using an ultrasonic homogenizer (SMT Co., Ltd., Cat. UH-50). 900 μL of mobile phase B was added to 100 μL of the cell homogenate, and the mixture was stirred for over 10 minutes. After centrifugation at 10000×g for 5 minutes, 250 μL of supernatant was collected into a polypropylene screw vial (GL Sciences Inc., Cat. 1030-61024) to prepare cell extracts.

(3) LC-MS/MS Measurement

The α-GalCer standard solutions prepared in (1) and the cell extracts prepared in (2) were measured by multiple reaction monitoring of LC-MS/MS. The measurement was carried out with the number of measurements set to 1 for the α-GalCer standard solutions and to 6, 3, or 1 for the cell extracts as shown in Table 1 of (5). LC employed 1200 series (Agilent Technologies, Inc.) was used as LC, and 6410 Triple Quad LC-MS (Agilent Technologies, Inc., Cat. G6410B) was used as MS. Samples were separated by LC. 10 μL each of the α-GalCer standard solutions and the cell extracts was applied to Accucore-150-C4 (Thermo Fisher Scientific Inc., Cat. 16526-103030) column, and the samples were separated using mobile phase A (0.1% formic acid) and mobile phase B (70% ethanol, 29.5% methanol, and 0.5% formic acid) on a gradient from 60% to 100% of the mobile phase B. The flow rate to the column was 0.4 ml/min, and the column temperature was 40° C. The separated solutions were sequentially introduced to MS, and compounds in the solutions were ionized by the electrospray ionization method. 858.7 [m/z] was selected as a precursor ion of α-GalCer from the generated ions. This precursor ion was further decomposed to detect 696.7 [m/z] as a product ion of α-GalCer. Values determined in advance by analyzing the α-GalCer standard solutions by the LC-MS/MS were used for the precursor ion and the product ion.

(4) Analysis

α-GalCer concentrations were quantified using analysis software (Agilent Technologies, Inc., Agilent MassHunter Quantitative Analysis). The retention time of α-GalCer was determined from results of measuring the α-GalCer standard solutions, and measurement samples were confirmed to exhibit a similar retention time, and the amount of α-GalCer in each of the measurement samples analyzed by the peak area method. A calibration curve was prepared from the results of analyzing the α-GalCer standard solutions prepared in (1), and the samples of interest were quantified. For the preparation of the calibration curve, measurement results obtained from 6 points of 1000 ng/mL, 500 ng/mL, 100 ng/mL, 50 ng/mL, 10 ng/mL, and 5 ng/mL or from 4 or 5 points among 6 points of 500 ng/mL, 100 ng/mL, 50 ng/mL, 10 ng/mL, 5 ng/mL, and 2.5 ng/mL were used.

(5) Results of Measuring α-GalCer Content

Results of measuring the amount of α-GalCer loaded on aAVC(3T3)-WT1 or aAVC-WT1 by LC-MS/MS are shown in the table below.

In Table 1, the three values shown at the α-GalCer addition concentration of 1500 ng/mL indicate the amount of α-GalCer loaded on the cells obtained in three independent experiments with different culture scales.

TABLE 1

| Type | α-GalCer addition concentration (ng/mL) | Amount loaded (ng/ $10^6$ cells) | The number of measurements |
|---|---|---|---|
| aAVC(3T3)-WT1 | 500 | 2.4* | 1 |
| aAVC-WT1 | 56 | 3.9* | 3 |
| | 167 | 10 | 3 |
| | 500 | 21 | 3 |
| | 1500 | 39 | 3 |
| | 1500 | 140 | 6 |
| | 1500 | 275 | 6 |
| | 3000 | 100 | 3 |

*represents "less than the lower limit value of quantification" when the number of the measured cells is $10^6$ cells.

Figure 1:
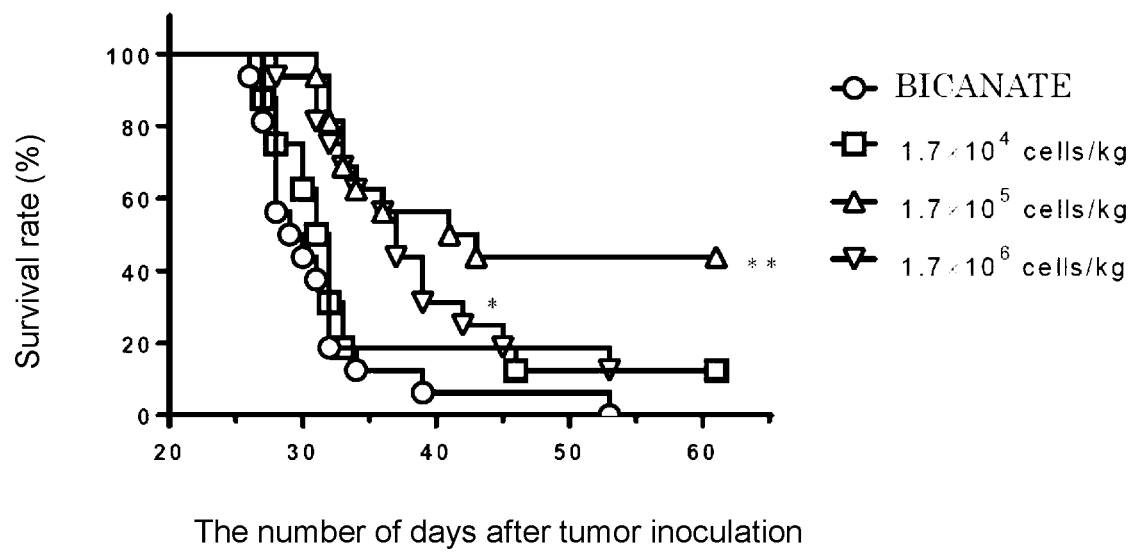
FIG. 1 shows a change in survival rate after administration of aAVC(3T3)-WT1 in a mouse lung metastasis model in which B16 melanoma cells were intravenously injected. B16-F10 cells were administered to the tail vein of each 7-week-old C57BL/6J female mice at $2 \times 10^4$ cells, and 3 hours after administration, BICANATE or each dose of aAVC(3T3)-WT1 was administered to the tail vein of the mice (n=16 in each group). The survival of the mice was examined for 61 days after the administration. The survival time of the aAVC(3T3)-WT1 administration group was compared with the survival time of the BICANATE administration group by use of the log-rank test to determine a significance probability P-value. In the drawing, * and ** indicate that P-value is less than significance levels 0.05/3 and 0.01/3, respectively, corrected by the Bonferroni's method.

Example 3: Determination of the Dose of aAVC(3T3)-WT1 Cells Showing Pharmacological Efficacy The antitumor effect by activation of NKT cells mediated by α-GalCer of aAVC(3T3)-WT1 was evaluated in a mouse lung metastasis model in which B16 melanoma cells were intravenously injected. B16-F10 melanoma cells (ATCC, Cat. CRL-6475) suspended in PBS were administered at $2\times10^4$ cells to the tail vein of each 7-week-old C57BL/6J female mouse (Charles River Laboratories Japan, Inc.) (n=16 in each group) to prepare a mouse lung metastasis model in which B16 melanoma cells were intravenously injected. 3 hours after the administration, aAVC(3T3)-WT1 suspended in BICANATE Injection (Otsuka Pharmaceutical Co., Ltd.) where the loaded amount of α-GalCer is 2.4 ng/$10^6$ cells (the uppermost part of Table 1 in Example 2) was administered at $1.7\times10^4$ cells/kg, $1.7\times10^5$ cells/kg, or $1.7\times10^6$ cells/kg to the tail veins of the mice. 200 μL of BICANATE Injection was administered to a control group. The results of examining survival over 61 days from the administration of B16-F10 showed that the median survival time of the control group was 29.5 days, whereas the median survival time of the aAVC(3T3)-WT1 administration group was 31.5 days for the $1.7\times10^4$ cells/kg administration group, 42.0 days for the $1.7\times10^5$ cells/kg administration group, and 37.0 days for the $1.7\times10^6$ cells/kg administration group. When the survival times were compared by the log-rank test, the survival time of the groups given aAVC(3T3)-WT1 administered at $1.7\times10^5$ cells/kg or $1.7\times10^6$ cells/kg was significantly prolonged as compared with the control group (FIG. 1). Accordingly, aAVC(3T3)-WT1 was found to be effective at $1.7\times10^5$ cells/kg for this model. It has been reported that the antitumor effect of cells having α-GalCer loaded thereon in this model is attenuated due to a deficiency of NKT cells in mice or depletion of NK cells (J. Immunolo.; 2007; 178: 2853-2861). Thus, the antitumor effect of aAVC (3T3)-WT1 shown in this model is thought to be mediated by the activation of NKT cells by α-GalCer loaded thereon.

Example 4: Amount of α-GalCer Loaded and NKT Cell Activation

In order to estimate the pharmacological effective dose of human-type aAVC-WT1 using mouse-type aAVC(3T3)-WT1, the ability to activate NKT cells in mice was measured for aAVC(3T3)-WT1 and each aAVC-WT1 described in Table 1 of Example 2, and compared. The dose of α-GalCer necessary for exerting a pharmacological effect mediated by NKT cell activation by the administration of aAVC-WT1 to a human was determined using the results obtained above. The proportion of NKT cells in spleen cells after administration of aAVC(3T3)-WT1 was measured as an index for the ability to activate NKT cells.

aAVC(3T3)-WT1 or each aAVC-WT1 loaded with the amount of α-GalCer given in Table 1 of Example 2, and suspended in BICANATE Injection was administered at $1.7\times10^4$ cells/kg, $1.7\times10^5$ cells/kg, or $1.7\times10^6$ cells/kg to the tail vein of each 5-week-old C57BL/6J female mouse (Charles River Laboratories Japan, Inc.) (n=3 in each group). 200 μL of BICANATE Injection was administered to a control group. 3 days after administration, the mouse was sacrificed, and the spleen was excised. Spleen cells were prepared from the excised spleen according to a general method. NKT cells included in the spleen cells were stained with α-GalCer-bound recombinant soluble dimeric mouse CD1d:Ig fusion (CD1d/Gal-dimer, Becton, Dickinson and Company, Cat. 557599), APC-conjugated anti-mouse IgG1 (Becton, Dickinson and Company, Cat. 560089) and FITC-conjugated anti-mouse CD19 (BioLegend, Inc., Cat. 115506), and measured by flow cytometry. The proportion of NKT cells was calculated by analyzing the proportion of CD1d/Gal-dimer-positive and CD19-negative cells in lymphocyte-fraction cells of a forward scatter and side scatter cytogram using FlowJo ver. 10.2 software (FlowJo, LLC). As a result, a tendency was shown that the proportion of NKT cells in spleen cells was increased in accordance with the increase of the amount of α-GalCer loaded on aAVC-WT1 and the increase of the number of administered cells (FIG. 2). These results suggest that the amount of α-GalCer administered is markedly strongly correlated with NKT cell activation rather than the number of administered cells.

The proportion of NKT cells in spleen cells was 1.1% (shaded bar of aAVC(3T3)-WT1 in FIG. 2) when aAVC (3T3)-WT1 was administered at $1.7\times10^5$ cells/kg (dose that significantly prolonged survival time as compared with a control group in Example 3). In the aAVC-WT1 administered mouse, the minimum dose of α-GalCer exhibiting an NKT cell proportion of 1.1% or more was 1.7 ng/kg (FIG. 2, shaded bar of aAVC-WT1 with α-GalCer 10 ng/$10^6$ cells; and Table 2, when 10 ng/$10^6$ cells of α-GalCer was administered at $1.7\times10^5$ cells/kg, 1.7 ng/kg was administered in term of a dose of the α-GalCer). This suggests that an α-GalCer dose of 1.7 ng/kg or more can significantly elevate the proportion of NKT cells in spleen cells.

Even the minimum amount of α-GalCer loaded on the aAVC cell surface, corresponding to a concentration of 3.9 ng/$10^6$ cells, showed an NKT cell proportion of 1.1% or more as long as the dose of α-GalCer was one exceeding 1.7 ng/kg (FIG. 2, filled bar graph of aAVC-WT1 wherein the amount of the loaded α-GalCer was 3.9 ng/$10^6$ cells). This suggests that it is desirable to use cells loaded with α-GalCer at a concentration of 3.9 ng/10⁶ cells or higher.

Table 2 summarizes the types of the cells, the amount of the loaded α-GalCer, the numbers of administered cells and the doses of α-GalCer in administration at said numbers of administered cells to mice, used in Examples 3 and 4.

TABLE 2

| Type | Amount of α-GalCer loaded (ng/10⁶ cells) | The number of administered cells (cells/kg) | α-GalCer dose (ng/kg) |
|---|---|---|---|
| aAVC(3T3)-WT1 | 2.4* | 1.7 × 10⁴ | 0.041 |
|  |  | 1.7 × 10⁵ | 0.41 |
|  |  | 1.7 × 10⁶ | 4.1 |
| aAVC-WT1 | 3.9* | 1.7 × 10⁴ | 0.066 |
|  |  | 1.7 × 10⁵ | 0.66 |
|  |  | 1.7 × 10⁶ | 6.6 |
|  | 10 | 1.7 × 10⁴ | 0.17 |
|  |  | 1.7 × 10⁵ | 1.7 |
|  |  | 1.7 × 10⁶ | 17 |
|  | 21 | 1.7 × 10⁴ | 0.36 |
|  |  | 1.7 × 10⁵ | 3.6 |
|  |  | 1.7 × 10⁶ | 36 |
|  | 39 | 1.7 × 10⁴ | 0.66 |
|  |  | 1.7 × 10⁵ | 6.6 |
|  |  | 1.7 × 10⁶ | 66 |
|  | 100 | 1.7 × 10⁴ | 1.7 |
|  |  | 1.7 × 10⁵ | 17 |
|  |  | 1.7 × 10⁶ | 170 |
|  | 140 | 1.7 × 10⁴ | 2.4 |
|  |  | 1.7 × 10⁵ | 24 |
|  |  | 1.7 × 10⁶ | 238 |
|  | 275 | 1.7 × 10⁴ | 4.7 |
|  |  | 1.7 × 10⁵ | 47 |
|  |  | 1.7 × 10⁶ | 468 |

*represents "less than the lower limit value of quantification" when the number of the measured cells is 10⁶ cells.

Example 5: Toxicity Study after Single-Dose Intravenous Administration in Mice Toxicity of aAVC-WT1 (amount of α-GalCer loaded: 275 ng/10⁶ cells) for after single-dose intravenous administration to mice was evaluated. Eight-week old C57BL/6J female or male mice (Charles River Laboratories Japan, Inc.) were used in each group consisting of five mice. As the administration group, four groups: a vehicle control group, a low-dose group (1×10⁶ cells/kg), a middle-dose group (1×10⁷ cells/kg) and a high-dose group (1×10⁸ cells/kg), were set. BICANATE Injection (Otsuka Pharmaceutical Co., Ltd.) was used as the vehicle to prepare the cell administration solution. aAVC-WT1 was suspended in BICANATE Injection to prepare 1×10⁵ cells/mL administration solution for the low-dose group, 1×10⁶ cells/mL administration solution for the middle-dose group, and 1×10⁷ cells/mL administration solution for the high-dose group, respectively. The dose to the mice was set to 10 mL/kg. The amount of the dosing solution was calculated for each mouse base on the body weight measured on the day of administration, and the vehicle or each cell dosing solution was administered once into the tail vein of each mouse. The mice after the administration were subjected to examination of general conditions and body weight measurement over 7 days after the administration. Then the mice was sacrificed on the 7 days of post-administration and subjected to necropsy. No effects (death, moribundity, other decrease in locomotor activity, etc.) due to administration of vehicle or each cell dosing solution were observed during the observation period of general conditions (observed 3 times in total before administration, 1 hour after administration, and 4 hours after administration on the day of administration, and once a day from the day after administration until necropsy). The body weight measurement was performed on the day before administration, on the day of administration, on the day after administration, 3 days and 7 days after administration. Decrease in body weight was found on 3 days after administration in females and males in the high-dose group (FIG. 3). In food consumption measurement (the food consumptions per day were measured from 3 days before administration to the day before administration, from the day of administration to the day after administration, from the day after administration to 3 days after administration, and from 3 days after administration to 7 days after administration), decrease in food consumption was found from the day of administration to the day after administration and from the day after administration to 3 days after administration in females in the middle-dose group and females and males in the high-dose group (FIG. 4). From the results of this study, no effects on body weight and food consumption was found in the low-dose group, therefore, it was considered that the dose of 1×10⁶ cells/kg is the upper limit of the dose that does not affect body weight and food consumption (equivalent to 275 ng/kg of α-GalCer dose calculated from the amount of α-GalCer loaded).

INDUSTRIAL APPLICABILITY

The present invention is expected to be useful in effective and safe treatment or prevention of a cancer using aAVC.

[Free Text of Sequence Listing]

"Artificial Sequence" will be described in the numeric caption <223> of the sequence listing given below.

The nucleotide sequence set force in SEQ ID NO: 1 of the sequence listing is a nucleotide sequence encoding human WT1 protein, and the amino acid sequence set force in SEQ ID NO: 2 of the sequence listing is an amino acid sequence encoded by the sequence of SEQ ID NO: 1. The nucleotide sequence set force in SEQ ID NO: 3 of the sequence listing is a nucleotide sequence encoding human CD1d protein, and the amino acid sequence set force in SEQ ID NO: 4 of the sequence listing is an amino acid sequence encoded by the sequence of SEQ ID NO: 3. The nucleotide sequence set force in SEQ ID NO: 5 of the sequence listing is a nucleotide sequence encoding mouse CD1d protein, and the amino acid sequence set force in SEQ ID NO: 6 of the sequence listing is an amino acid sequence encoded by the sequence of SEQ ID NO: 5.

[Sequence Listing]

The invention claimed is:

1. A method for treating a cancer, comprising administering a human-derived cell to a human,
wherein the cell expresses exogenous CD1d and has α-galactosylceramide (α-GalCer) loaded on the cell surface,
wherein the cell expresses an exogenous cancer antigen,
and wherein the cell is administered to the human such that a single dose of α-GalCer loaded on the cell surface ranges from 1.7 ng to 275 ng per kg body weight of the human,
wherein the amount of α-GalCer loaded on the cell surface is in the range of 3.9 to 275 ng per $1 \times 10^6$ cells.

2. The method according to claim 1, wherein the CD1d is human CD1d.

3. The method according to claim 1, wherein the human-derived cell is a human embryonic kidney cell 293 (HEK293)-derived cell.

* * * * *